(12) United States Patent
Berberich et al.

(10) Patent No.: US 10,449,534 B2
(45) Date of Patent: Oct. 22, 2019

(54) CONTROL UNIT FOR PIPETTING MACHINES

(71) Applicant: BRAND GMBH + CO KG, Wertheim (DE)

(72) Inventors: Christian Berberich, Neunkirchen (DE); Jürgen Schraut, Rettersheim (DE); Michael Zugelder, Darmstadt (DE); Thomas Howe, Wertheim (DE)

(73) Assignee: BRAND GMBH + CO KG, Wertheim (DE)

( * ) Notice: Subject to any disclaimer, the term of this patent is extended or adjusted under 35 U.S.C. 154(b) by 0 days.

(21) Appl. No.: 14/941,931

(22) Filed: Nov. 16, 2015

(65) Prior Publication Data

US 2016/0139166 A1    May 19, 2016

(30) Foreign Application Priority Data

Nov. 17, 2014   (EP) ..................................... 14003862

(51) Int. Cl.
　　*G01N 35/10* (2006.01)
　　*G01N 35/00* (2006.01)
　　*B01L 3/02* (2006.01)

(52) U.S. Cl.
　　CPC ......... *B01L 3/021* (2013.01); *B01L 2200/025* (2013.01); *B01L 2200/087* (2013.01);
　　(Continued)

(58) Field of Classification Search
　　None
　　See application file for complete search history.

(56) References Cited

U.S. PATENT DOCUMENTS 6,326,147 B1    12/2001    Oldham et al.
7,247,277 B1    7/2007    Inoue et al.
(Continued)

FOREIGN PATENT DOCUMENTS

DE    103 53 838 A1    6/2004
DE    601 32 100 T2    12/2008
(Continued)

OTHER PUBLICATIONS

Microlab Mimbus Instinct (Hamilton Robotics; 2 pages; Jan. 2012).*
(Continued)

*Primary Examiner* — Benjamin R Whatley
(74) *Attorney, Agent, or Firm* — David S. Safran; Roberts Mlotkowski Safran Cole & Calderon, P.C.

(57) ABSTRACT

A control unit for controlling a pipetting machine a pipetting machine, and a method for controlling a pipetting machine, wherein the control unit controls at least one actuator for moving a pipetting device between receptacle units for liquids to be pipetted and for receiving or dispensing liquids to be pipetted. The control unit, by selecting one or more graphic receptacle unit equivalents which correspond to receptacle units, assigns at least one transfer parameter to the receptacle unit equivalents. The transfer parameter corresponds to a transfer volume, which is to be received from the receptacle unit corresponding to the respective receptacle unit equivalent or is to be dispensed into the receptacle unit corresponding to the respective receptacle unit equivalent. The control unit is additionally designed so that selected source receptacle unit equivalents are simultaneously assignable to multiple target receptacle unit equivalents.

13 Claims, 18 Drawing Sheets

(52) U.S. Cl.
CPC ... *B01L 2200/143* (2013.01); *B01L 2300/024* (2013.01); *B01L 2300/027* (2013.01); *B01L 2300/0822* (2013.01); *B01L 2300/0829* (2013.01)

(56) References Cited

U.S. PATENT DOCUMENTS

| | | | |
|---|---|---|---|
| 7,998,751 B2* | 8/2011 | Evers | B01F 11/0071 422/500 |
| 2004/0096365 A1* | 5/2004 | Toi | G01N 35/1011 422/502 |
| 2004/0133288 A1 | 7/2004 | Hatcher et al. | |
| 2006/0048846 A1* | 3/2006 | Roenneburg | G01N 30/88 141/130 |
| 2006/0190840 A1* | 8/2006 | Frost, III | B01L 3/021 715/810 |
| 2006/0281183 A1* | 12/2006 | Sun | G01N 35/0092 436/43 |
| 2010/0126286 A1* | 5/2010 | Self | G01N 35/04 73/863.81 |
| 2011/0160909 A1* | 6/2011 | Glauser | G01N 35/00722 700/264 |
| 2013/0029856 A1* | 1/2013 | Kelso | G01N 35/028 506/7 |
| 2015/0100155 A1* | 4/2015 | Hren | G05B 11/01 700/244 |
| 2016/0319329 A1* | 11/2016 | Natale | G01N 35/028 |

FOREIGN PATENT DOCUMENTS

| | | |
|---|---|---|
| EP | 2 613 155 A1 | 7/2013 |
| EP | 2 713 166 A1 | 4/2014 |
| JP | 2000-093786 A | 4/2000 |
| WO | 2006/130826 A1 | 12/2006 |
| WO | WO 2015038910 A1 * | 3/2015 ........... G01N 35/028 |

OTHER PUBLICATIONS

Beckman Coulter quick start guide (Beckman Coulter Biomek 3000 User Guide; 48 pages; Feb. 2010).*

Beckman Coulter quick start guide 2 (Beckman Coulter Biomek 3000 quick start Guide; 52 pages; Dec. 2009).*

* cited by examiner

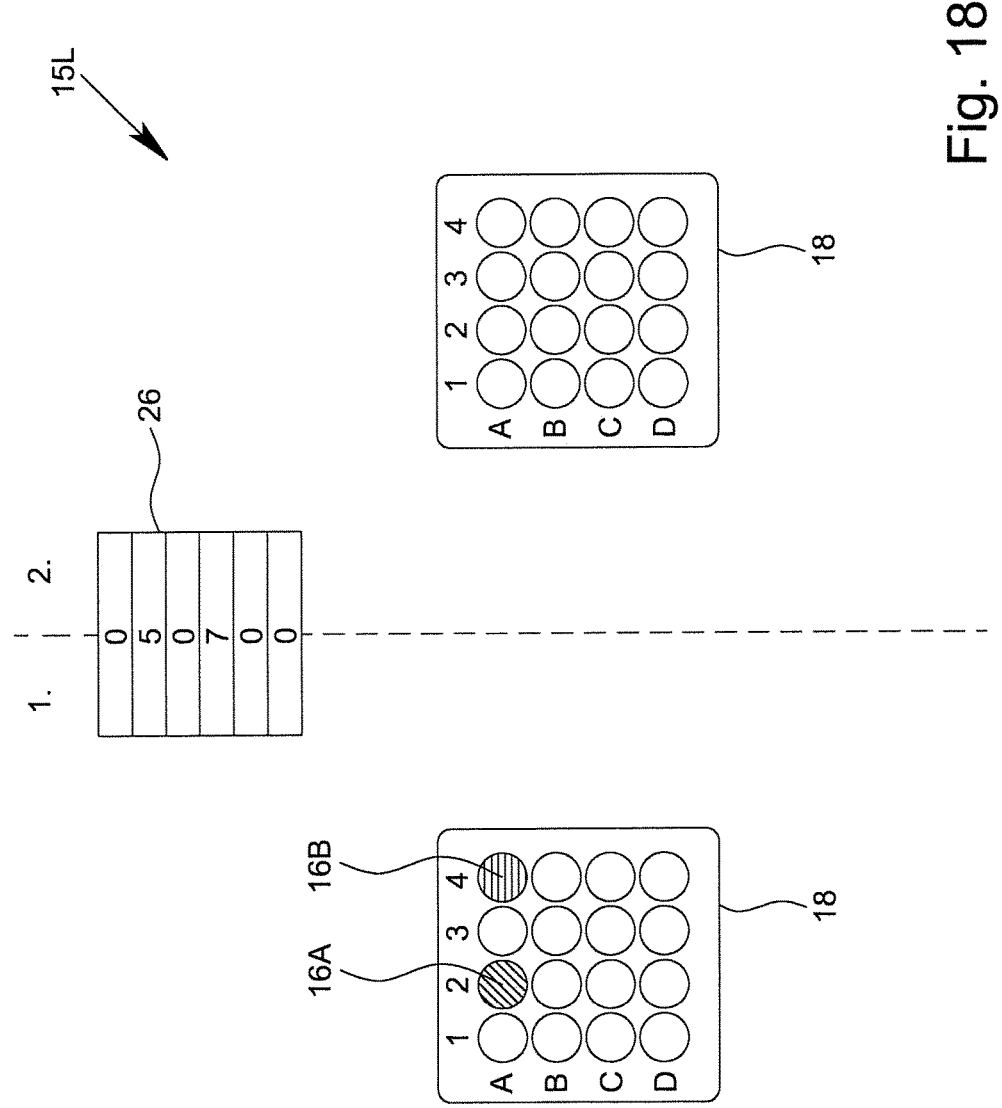

CONTROL UNIT FOR PIPETTING MACHINES

BACKGROUND OF THE INVENTION

Field of the Invention

The invention relates to a control unit for controlling a pipetting machine, a pipetting machine, and a method for controlling a pipetting machine in which the control unit is designed for controlling at least one actuator for moving a pipetting device between receptacle units for liquids to be pipetted, for receiving liquids to be pipetted, and/or for dispensing liquids to be pipette.

Description of Related Art

A pipetting machine in the meaning of the present invention is preferably a device, which is designed for fully automatic liquid transfer. For this purpose, the pipetting machine preferably has a pipetting device, which is movable in multiple spatial directions. Fundamentally, the proposed control unit can also be used for other devices, however, in particular for other laboratory machines, in particular for repositioning of substances or objects.

A pipetting machine of the type under discussion is preferably designed to move a pipetting device, also called a pipetting head or liquid end, between different operating positions. For this purpose, the pipetting machine can have a positioning unit, in particular an X-/Y-/Z-movement unit, by which the pipetting device can be moved. The positioning unit can also be or have a robot arm, by which the pipetting device is movable at least substantially freely in space.

A pipetting device in the meaning of the present invention is preferably a movable head having one or more displacer units or other units for generating overpressure or underpressure for aspirating or expelling liquids. The pipetting device preferably has one or more coupling points for attaching or replacing one or more pipette tips or syringes. The respective pipette tips or coupling points are associated, preferably in each case, with displacer units. The syringe or the respective syringes is/are preferably designed as a displacer unit or form such a unit.

The pipetting device can have one or more pipette tips or syringes at one or more coupling points, wherein pipetting devices having only a single pipette tip or syringe are referred to as a single-channel pipetting device and a pipetting device having multiple pipette tips or syringes is referred to as a multichannel pipetting device.

Displacer unit(s) of the pipetting device usually has/have one or more cylinder-and-piston arrangements, which are designed to aspirate liquid through the discharge opening(s) of the pipette tip(s) therein or to expel it therefrom. Fundamentally, aspirating and expelling of liquid into or out of the respective pipette tip, can also be performed in another manner, however.

The pipetting machine preferably has receptacle units for liquids to be pipetted or is designed to accommodate or hold such receptacle units, in particular so-called cells, wells, or the like.

The pipetting machine preferably has one actuator or multiple actuators, by means of which the pipetting device is moved or is movable between different receptacle units, and/or by means of which the receiving of liquid in and/or the dispensing of liquid from one or more of the pipette tips of the pipetting device can be caused. These or further actuators of the pipetting machine are preferably controllable by a control unit.

An actuator in the meaning of the present invention is preferably a unit for the controlled performance of an effect for operating the pipetting machine. In particular, the actuator is a motor or another drive for moving the pipetting device and/or a drive for moving the piston of a cylinder-and-piston arrangement or other displacer unit, to aspirate liquid through a discharge opening of a pipette tip therein or to expel it therefrom.

European Patent Application EP 2 613 155 A1 and corresponding U.S. Pat. No. 8,580,197 disclose a control unit for a computer-controlled pipetting machine. The pipetting machine comprises a work surface for arranging containers and a motorized pipetting robot. The pipetting robot has at least one pipette for receiving and dispensing liquid samples. The control unit is set up to control the pipetting robot, so that it can position the at least one pipette at specific positions on the work surface.

The known pipetting machine furthermore comprises an interface, which has input means and display means. Multiple configuration interfaces can be displayed by the display means.

The known control unit is designed, by way of selection of one or more pictograms, which correspond to containers, to assign a desired volume to the pictograms by means of the input means, which is to be received from the container corresponding to the respective pictogram or is to be dispensed to the container corresponding to the respective pictogram.

U.S. Pat. No. 6,694,197 discloses a control unit for a single-channel reformatting device. With the aid of this reformatting device, liquids can be transferred from cells, which receive the liquids of a source plate to cells of a target plate. For this purpose, the known control unit controls an x-y-positioning unit and a z-positioning unit.

By means of the x-y-positioning unit, an arbitrary cell of the source plate or target plate can be positioned under a pipetting device for receiving or dispensing liquid to be pipetted. By means of the z-positioning unit, the pipetting device can be moved vertically upward and downward.

By way of a graphic user interface, pictograms of source plates and target plates and the cells thereof can be displayed in a configuration interface. The pictograms of the plates and the cells thereof can be selected by clicking. By selecting a cell of the source plate and subsequently selecting one or more cells of the target plate a linkage between the cells can be specified. In addition, transfer parameters like a volume to be transferred can be defined.

SUMMARY OF THE INVENTION

The present invention is based on the problem of specifying a control unit for controlling a pipetting machine, a pipetting machine having such a control unit, and a method for controlling a pipetting machine, whereby a user-friendly, more rapid, and resource-conserving operating mode, which is less susceptible to error, is enabled.

The above-described problem is solved by a control unit, a pipetting machine and a method for controlling a pipetting machine having the features described herein.

A first aspect of the present invention relates to a control unit for controlling a pipetting machine, in particular a pipetting machine having the features described at the outset. The control unit is designed for controlling at least one actuator of the pipetting machine, in particular for moving a pipetting device between receptacle units for receiving or dispensing liquids to be pipetted. Alternatively or additionally, the actuator is designed for receiving and/or for dispensing liquids to be pipetted, in particular by generating an underpressure or overpressure in the pipetting device.

The control unit for controlling the pipetting machine has an input unit and a display unit. Alternatively or additionally, the control unit has at least one storage unit, in particular a working memory and/or a read-only memory such as a hard drive, and/or a processor. Furthermore, the control unit preferably has an interface, which is designed to control the actuator or actuators of the pipetting machine.

An input unit in the meaning of the present invention is preferably a keyboard, a computer mouse, a trackball, a touchscreen, a camera, a sensor, or another unit for controlling a or for data input into a computer or the like.

A display unit is preferably a monitor, a display screen, a touchscreen, a projector, or another unit for displaying a graphic user interface, in particular one or more configuration interfaces.

One or more different configuration interfaces are displayable by the display unit.

One or more graphic receptacle unit equivalents, which each represent at least one receptacle unit and correspond to receptacle units, are displayable on the display unit in a configuration interface.

A receptacle unit in the meaning of the present invention is preferably a vessel, a recess, indentation, depression, and/or predefined position, wherein the receptacle unit is designed to receive and provide liquid to be pipetted.

The control unit is designed, by way of selecting one or more graphic receptacle unit equivalent(s) by means of the input unit, preferably in the same configuration interface, to associate at least one transfer parameter with the receptacle unit equivalent(s). The transfer parameter corresponds to a transfer volume, which is to be received from the receptacle unit corresponding to the respective receptacle unit equivalent, or is to be dispensed to the receptacle unit corresponding to the respective receptacle unit equivalent.

A graphic receptacle unit equivalent in the meaning of the present invention is preferably a graphic means for representing at least one receptacle unit in a configuration interface, which is displayable or displayed by the display unit. The respective receptacle unit equivalent preferably corresponds to a specific receptacle unit of the pipetting machine, in particular in its shape and/or position or location in relation to other receptacle units or receptacle unit equivalents. The receptacle units of the pipetting machine to be controlled are particularly preferred schematically displayed, displayable, or represented by means of the receptacle unit equivalents in the configuration interface.

A transfer parameter in the meaning of the present invention is preferably a value, in particular a dimensioned number, or the like. The transfer parameter preferably corresponds to a transfer volume.

The transfer volume is preferably a specific liquid volume, which is to be received from the respective receptacle unit or is to be dispensed to the respective receptacle unit. The transfer volume can be one to be received or removed, i.e., a volume of the liquid to be pipetted which is to be removed from a receptacle unit and/or is to be received in a pipette tip or syringe, in particular to be aspirated. The terms transfer volumes "to be received" and "to be removed" are preferably synonymous and exchangeable. Alternatively or additionally, the transfer volume can be a volume to be dispensed, i.e., a volume to be conveyed from a pipette tip or syringe and/or a volume to be dispensed into the receptacle unit, of the liquid to be pipetted. Transfer volumes to be received and dispensed can be distinguished, for example, by way of a sign or another identifier of the transfer parameter or transfer volume.

According to the invention, the control unit is designed so that multiple receptacle unit equivalents, from the corresponding receptacle units of which liquid is to be removed, are selectable successively or simultaneously as source receptacle unit equivalents of a source pipetting unit equivalent. The selected source receptacle unit equivalents are simultaneously assignable to multiple further receptacle unit equivalents as target receptacle unit equivalents of a target pipetting unit equivalent, into the corresponding receptacle units of which liquid is to be dispensed, such that the arrangement and/or number of the assigned target receptacle unit equivalents differs from the arrangement and/or number of the selected source receptacle unit equivalents.

Transfer parameters are thus assigned to the selected source receptacle unit equivalents and the target receptacle unit equivalents assigned thereto such that in each case the corresponding transfer volume from the receptacle units corresponding to the selected source receptacle unit equivalents is transferable into the receptacle units corresponding to the assigned target receptacle unit equivalents.

The proposed control unit is designed so that the assigned target receptacle unit equivalents are displayable in the same configuration interface as the selected source receptacle unit equivalents.

The proposed control unit offers the advantage of a comfortable, rapid, and reliable control of the pipetting machine. In particular, using the proposed control unit, a transfer pattern can be created and changed conveniently and rapidly, and can be assigned to multiple target receptacle unit equivalents simultaneously.

A transfer pattern is understood here as a graphic representation of receptacle unit equivalents, which depicts how source receptacle unit equivalents are assigned to target receptacle unit equivalents. A transfer pattern thus represents an assignment rule. A transfer pattern can be predefined, for example, by means of an input unit. A transfer pattern can also be generated in that firstly source receptacle unit equivalents are selected, wherein firstly a graphic representation or marking of the selected source receptacle unit equivalents is performed. The graphic representation or marking can then be changed with respect to the number and arrangement of the receptacle unit equivalents. Finally, multiple target receptacle unit equivalents can be selected on the basis of the graphic representation or marking. By way of the selection, the source receptacle unit equivalents are assigned to the target receptacle unit equivalents, whereby transfer parameters are assigned to the selected source receptacle unit equivalents and their assigned target receptacle unit equivalents such that in each case the corresponding transfer volume is transferable from the receptacle units corresponding to the source receptacle unit equivalents into the receptacle units corresponding to the assigned target receptacle unit equivalents.

The present invention is thus based on the concept that liquid is transferable between a specifiable selection of receptacle units and in this case the assignment thereof can be performed simultaneously via a configuration interface.

A further aspect of the present invention, which is also implementable independently, relates to a control unit for controlling a pipetting machine, which is designed for controlling at least one actuator for moving a pipetting device between receptacle units for liquids to be pipetted and for receiving or dispensing liquids to be pipetted. The control unit has an input unit and a display unit, wherein multiple configuration interfaces are displayable by the display unit.

The control unit is designed, by selecting one or more graphic receptacle unit equivalents by means of the input unit, to assign to the receptacle unit equivalents at least one transfer parameter, which corresponds to a transfer volume, which is to be received from the receptacle unit corresponding to the respective receptacle unit equivalent or is to be dispensed to the receptacle unit corresponding to the respective receptacle unit equivalent.

According to the invention, multiple receptacle unit equivalents, from the corresponding receptacle units of which liquid is to be removed, are successively or simultaneously selectable as source receptacle unit equivalents of a source pipetting unit equivalent. The selected source receptacle unit equivalents can be divided into at least two subgroups. These subgroups are successively assignable to further receptacle unit equivalents as target receptacle unit equivalents of a target pipetting unit equivalent, into the corresponding receptacle units of which liquid is to be dispensed. In this case, all source receptacle unit equivalents of each subgroup are simultaneously assignable to the respective target receptacle unit equivalents.

Transfer parameters are thus assigned to the selected source receptacle unit equivalents and their assigned target receptacle unit equivalents such that in each case the corresponding transfer volume is transferable from the receptacle units corresponding to the selected source receptacle unit equivalents into the receptacle units corresponding to the assigned target receptacle unit equivalents.

The assigned target receptacle unit equivalents are displayable in this case in the same configuration interface as the selected source receptacle unit equivalents.

The proposed control unit offers the advantage of a convenient, rapid, and reliable control of the pipetting machine. In particular, smaller subgroups from a large group of selected source receptacle unit equivalents can be assigned step-by-step to multiple target receptacle unit equivalents, without performing a further selection of source receptacle unit equivalents.

This aspect of the invention can advantageously be combined with the features explained above of the first independent aspect. Thus, for example, after the division into subgroups, the arrangement and/or number of the receptacle unit equivalents of one or all subgroup(s) can be changed, before the receptacle unit equivalents of these subgroup(s) are assigned.

A further aspect of the present invention, which is also implementable independently, relates to a pipetting machine having one of the above-described control units, wherein the pipetting machine has at least one actuator, which is controllable by the control unit, for moving the pipetting device between the receptacle units.

A further aspect of the present invention, which is also implementable independently, relates to a method for controlling the pipetting machine for controlling at least one actuator for moving the pipetting device between receptacle units for liquids to be pipetted, for receiving liquids to be pipetted, and/or for dispensing liquids to be pipetted, by means of a control unit, which has an input unit and a display unit. Multiple configuration interfaces are displayable by the display unit.

In the proposed method, by selecting one or more graphic receptacle unit equivalent(s) by means of the input unit, at least one transfer parameter is assigned to the receptacle unit equivalent(s), the transfer parameter corresponding to a transfer volume, which is to be received from the receptacle unit corresponding to the respective receptacle unit equivalent or is to be dispensed to the receptacle unit corresponding to the respective receptacle unit equivalent.

In the proposed method, multiple receptacle unit equivalents, from the corresponding receptacle units of which liquid is to be removed, are successively or simultaneously selected as source receptacle unit equivalents of a source pipetting unit equivalent. The selected source receptacle unit equivalents are all simultaneously assigned to multiple further receptacle unit equivalents as target receptacle unit equivalents of a target pipetting unit equivalent, into the corresponding receptacle units of which liquid is to be dispensed, such that the arrangement and/or number of the assigned target receptacle unit equivalents differs from the arrangement and/or number of the selected source receptacle unit equivalents.

Transfer parameters are thus assigned to the selected source receptacle unit equivalents and their assigned target receptacle unit equivalents such that in each case the corresponding transfer volume is transferred from the receptacle units corresponding to the selected source receptacle unit equivalents into the receptacle units corresponding to the assigned target receptacle unit equivalents.

The assigned target receptacle unit equivalents are displayed in this case in the same configuration interface as the selected source receptacle unit equivalents.

A further aspect of the present invention, which is also implementable independently, relates to a method for controlling the pipetting machine for controlling at least one actuator for moving the pipetting device between receptacle units for liquids to be pipetted, for receiving liquids to be pipetted, and/or for dispensing liquids to be pipetted, by means of a control unit, which has an input unit and a display unit. Multiple configuration interfaces are displayable by the display unit.

In the proposed method, by selecting one or more graphic receptacle unit equivalent(s) by means of the input unit, at least one transfer parameter is assigned to the receptacle unit equivalent(s), the transfer parameter corresponding to a transfer volume, which is to be received from the receptacle unit corresponding to the respective receptacle unit equivalent or is to be dispensed to the receptacle unit corresponding to the respective receptacle unit equivalent.

In the proposed method, multiple receptacle unit equivalents, from the corresponding receptacle units of which liquid is to be removed, are successively or simultaneously selected as source receptacle unit equivalents of a source pipetting unit equivalent. The selected source receptacle unit equivalents are divided into at least two subgroups. These subgroups are successively assigned to further receptacle unit equivalents as target receptacle unit equivalents of a target pipetting unit equivalent, into the corresponding receptacle units of which liquid is to be dispensed. In this case, all source receptacle unit equivalents of each subgroup are simultaneously assigned to the respective target receptacle unit equivalents.

Transfer parameters are thus assigned to the selected source receptacle unit equivalents and their assigned target receptacle unit equivalents such that in each case the corresponding transfer volume is transferred from the receptacle units corresponding to the selected source receptacle unit equivalents into the receptacle units corresponding to the assigned target receptacle unit equivalents.

The assigned target receptacle unit equivalents are displayed in this case in the same configuration interface as the selected source receptacle unit equivalents.

The above-mentioned aspects and features can be implemented independently of one another, in particular independently of other features of the independent patent claims, but also in any arbitrary combination.

Further advantages, features, characteristics, and aspects of the present invention will become apparent from the following description with reference to the accompanying drawings.

BRIEF DESCRIPTION OF THE DRAWINGS

FIG. 18 shows a schematic illustration of a twelfth configuration interface of the proposed control unit.

DETAILED DESCRIPTION OF THE INVENTION

The same reference signs are used for identical or similar parts or elements in the figures, wherein identical or similar characteristics can be achieved, even if a repeated description is omitted.

Figure 1:
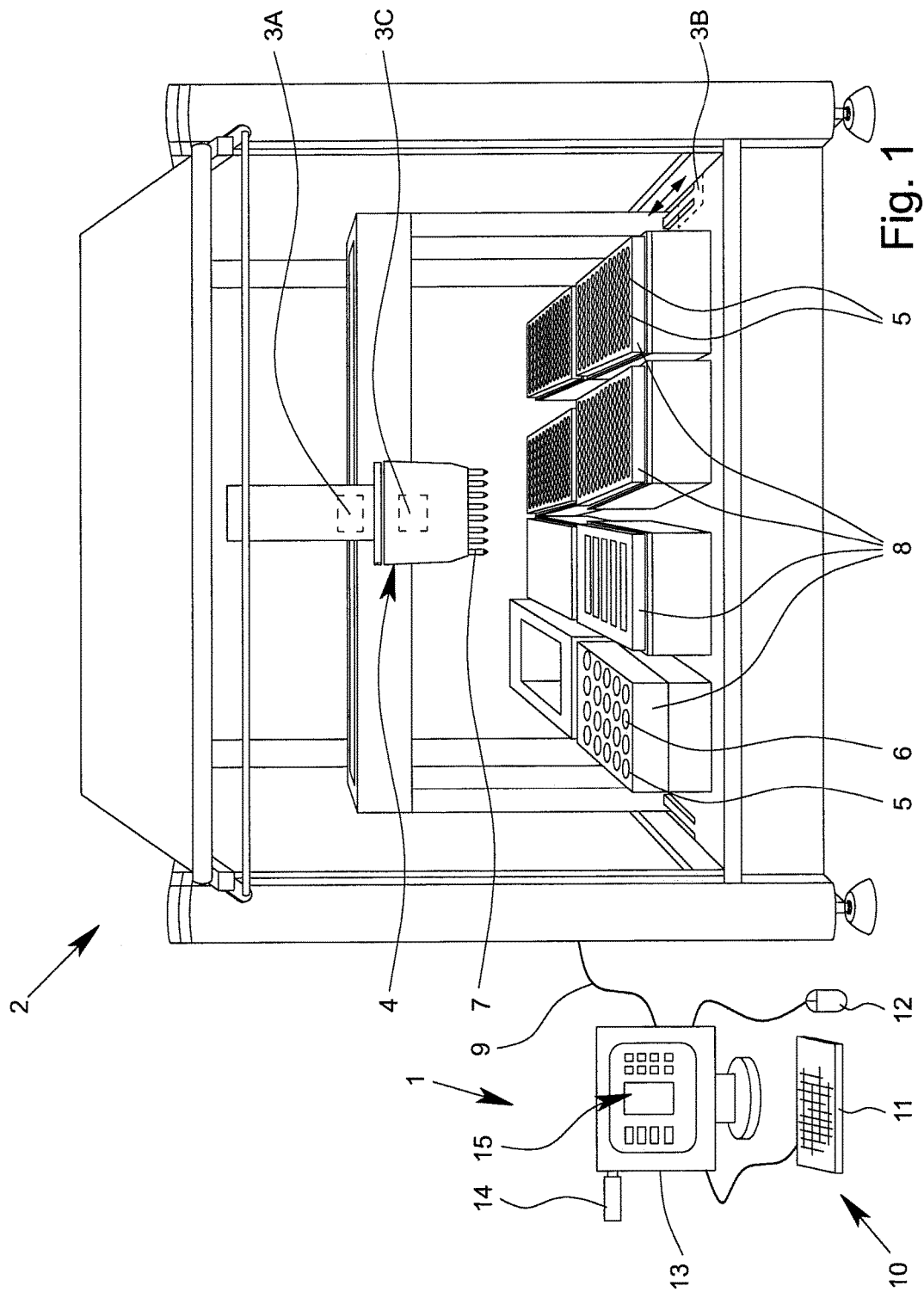
FIG. 1 shows a schematic illustration of a proposed pipetting device having a proposed control unit.

FIG. 1 shows a schematic illustration of a proposed control unit 1 for controlling a pipetting machine 2. The control unit 1 is designed for controlling at least one actuator 3A, 3B, or 3C of the pipetting machine 2.

The control unit 1 is designed for moving one or more of the actuators 3A, 3B, 3C for moving a pipetting device 4 between receptacle units 5 for liquids 6 to be pipetted. Alternatively or additionally, it is provided that the control unit 1 can control one or more of the actuators 3A, 3B, 3C such that liquids 6 to be pipetted can be received or dispensed using the pipetting device 4.

In the illustrated example, the actuators 3A, 3B form a positioning unit for changing the position of the pipetting device 4, preferably in all three spatial directions. The actuator 3C is preferably designed as a drive for a cylinder-and-piston unit for aspirating and dispensing liquid. However, there are also alternative variants here.

The pipetting device 4 is a multichannel pipetting device in the illustrated example, which preferably has multiple pipette tips 7 or is designed to remove liquid 6 from multiple adjacent receptacle units 5 or dispense it into adjacent receptacle units 5. However, the pipetting device 4 can also be a single-channel pipetting device 4, in which only one pipette tip 7 is provided.

The pipetting machine 2 can be designed so that the pipetting device 4 is replaceable, in particular to change between a single-channel pipetting device 4 and a multichannel pipetting device 4.

The pipetting device 4 preferably has the actuator 3C and is designed in this way or in another manner for receiving liquid 6 in the pipette tip(s) 7 or dispensing liquid therefrom. This is performed in particular by way of the above-mentioned cylinder-and-piston unit or another displacement mechanism, which can be drivable by the actuator 3C.

The pipetting machine 2 preferably has one or more pipetting units 8, which each have multiple receptacle units 5. The pipetting units 8 are preferably arrangeable at predefined positions in the pipetting machine 2. Receptacles, holders, or position markings are preferably provided for this purpose. Furthermore, the pipetting units 8 can optionally be furnished or provided with, in particular different spacers, to set a distance of the receptacle units 5 to the pipetting device 4 or the pipette tip(s) 7.

The pipetting units 8 are in particular so-called microtitration plates, PCR plates, deep well plates, and/or slides. The receptacle units 5 are particularly preferably designed as vessels, containers, cavities, recesses, or the like, in particular for receiving liquids or having a volume in the microliter range. Alternatively or additionally, the receptacle units 5, however, can also be surface portions for depositing a drop, which are preferably marked accordingly or have a surface coating or structuring, which is different from the regions surrounding the respective receptacle unit 5.

The control unit 1 is preferably connected to the pipetting machine 2 via a data interface 9. In this way, the control unit 1 can communicate with the pipetting machine 2, retrieve sensor data from the pipetting machine 2 or receive sensor data from the pipetting machine 2, and/or transmit control signals to the pipetting machine 2, in particular for controlling one or more of the actuators, 3A, 3B, 3C.

The control unit 1 preferably has one or more input units 10, in particular a keyboard 11 and/or a computer mouse 12. Furthermore, the control unit 1 preferably has a display unit 13, in particular a display screen or a touch display screen. The sensor of a touch display screen can function as an input unit 10 alternatively or additionally to the keyboard 11 and the computer mouse 12.

The control unit 1 preferably has a computer-readable storage medium 14, on which a program for controlling the pipetting machine 2 can be stored. The control unit 1, however, can also be connected to a server, in particular via the Internet, wherein a computer program product having program code means, which are designed to control the pipetting machine 2, is retrievable or executable remotely, in particular as a so-called client-server application. Furthermore, the control unit 1 preferably has a processor or controller, to execute a program for controlling the pipetting machine 2.

The control unit 1 is preferably designed to generate one or more configuration interfaces 15 and/or to display them by means of the display unit 13. The configuration interfaces 15 are preferably designed and set up to configure a control of the pipetting machine 2 by means of the control unit 1 or make it configurable. The control unit 1 is particularly preferably designed to generate one or more different configuration interfaces 15, which will be discussed in detail in the following figures.

Figure 2:
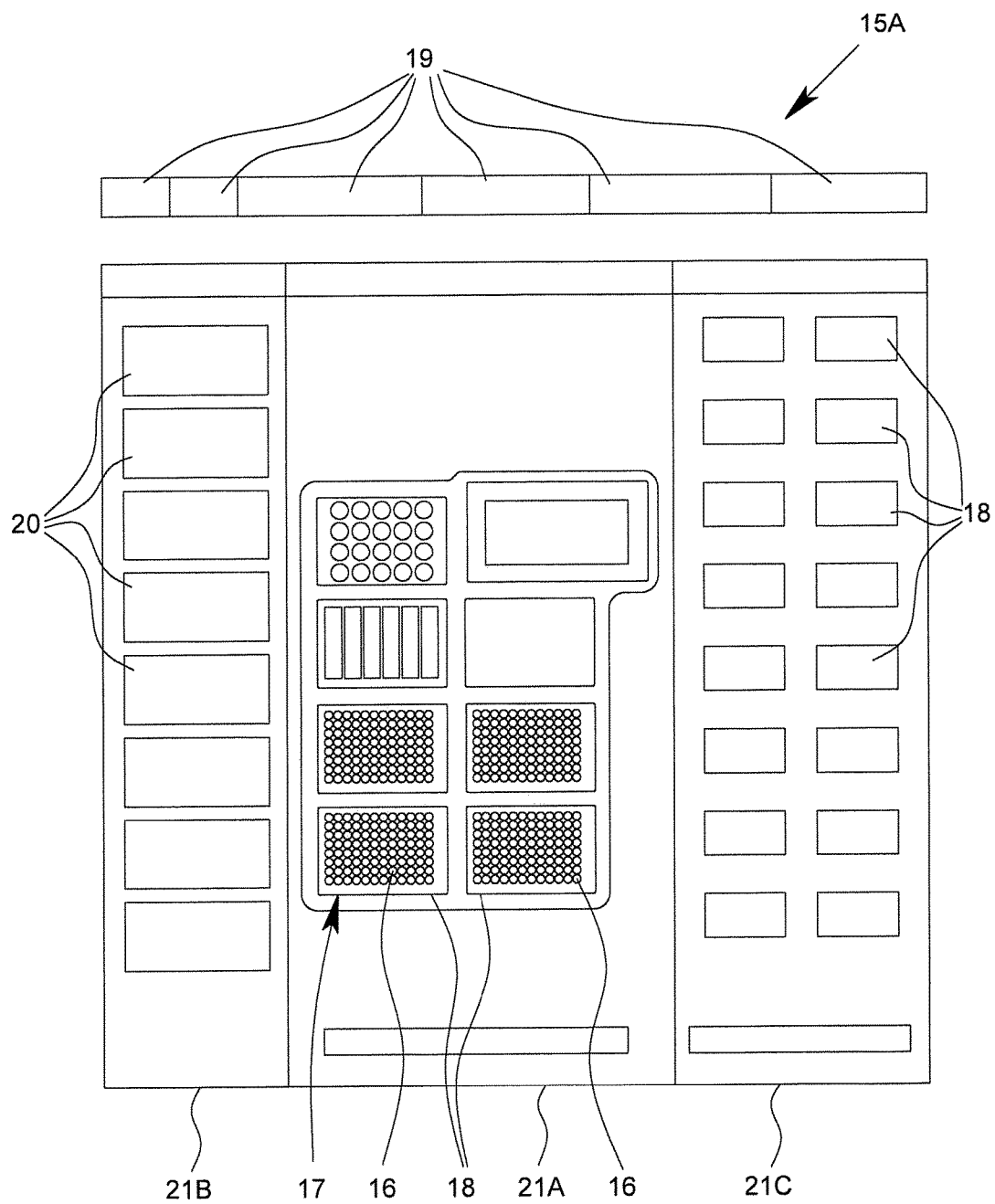
FIG. 2 shows a schematic illustration of a first configuration interface of the proposed control unit.

FIG. 2 shows a schematic illustration of a first configuration interface 15A of the proposed control unit 1. Multiple graphic receptacle unit equivalents 16 are preferably displayed in the configuration interface 15A.

The receptacle unit equivalents 16 preferably each correspond to receptacle units 5, which are arranged or arrangeable in the pipetting machine 2. In particular, it is provided that the receptacle unit equivalents 16 reflect or represent the arrangement of the receptacle units 5 in the pipetting machine 2. For this purpose, it can be provided that the receptacle unit equivalents 16 are each schematic illustrations of the receptacle units 5 or are suitable in another way for representing or marking a receptacle unit 5 and, preferably, the position of the receptacle unit 5 in relation to the other receptacle units 5.

It is preferably provided in the configuration interface 15A that by controlling via the input unit 10 receptacle unit equivalents 16 are selectable for different virtual positions 17, wherein the receptacle unit equivalents 16 correspond in their position or location and/or characteristic to the receptacle units 5, which are provided in the pipetting machine 2.

Corresponding to pipetting units 8, multiple receptacle unit equivalents 16 are particularly preferred each combined to form graphic pipetting unit equivalents 18, in particular in the form of a graphic representation of a plate, microtitration plate, PCR plate, deep well plate, and/or a plate having slides. The pipetting unit equivalents 18 preferably correspond to pipetting units 8, which is/are arranged or arrangeable in the pipetting machine 2. Preferably, pipetting unit equivalents 18 are selectable in the first configuration interface 15A and/or positionable at one or more of the virtual positions 17.

It can be provided that, by positioning receptacle units 5 or pipetting units 8 in the pipetting machine 2, corresponding receptacle unit equivalents 16 or corresponding pipetting unit equivalents 18 can automatically be provided or arranged at the corresponding virtual positions 17. For this purpose, the pipetting machine 2 can have one or more sensors and can transmit corresponding information or provide them for retrieval via the data interface 9, so that the control unit 1 adapts the configuration interface 15A fully automatically. The positioning of pipetting unit equivalents 18 or receptacle unit equivalents 16 at virtual positions 17 of the configuration interface 15A can also be performed manually or in another manner, however.

The configuration interface 15A is preferably configured with switchover means 19 to be switchable between different functions. In particular, it is provided that the control unit 1, as a response to an input using the input unit 10, changes or adapts the configuration interface 15A by activation of one of the switchover means 19 such that the receptacle unit equivalents 16 and/or pipetting unit equivalents 18 arranged at the virtual positions 17 are selectable, to enable a configuration in detail hereafter, also referred to as the configuration or setup mode. Such a configuration or setup mode is, for example, shown in FIG. 3.

Alternatively or additionally, the configuration interface 15A can be switched over into a programming mode, a simulation mode, and/or an execution mode, wherein in the programming mode basic functions or employed pipetting devices 4 can be settable, in the simulation mode the configuration interface 15A is designed to display the sequence and/or the result of a control of the pipetting machine 2, and/or wherein in the execution mode the pipetting machine 2 is controlled using the control unit 1 in a previously configured manner.

The configuration interface 15A is preferably furthermore designed to display intended occupations of the virtual positions 17 via configuration displays 20 and optionally additional information thereto. In this way, a comprehensible configuration and monitoring are possible in an advantageous manner.

The first configuration interface 15A preferably has multiple display portions 21A, 21B, and 21C. The pipetting unit equivalents 18 and/or the receptacle unit equivalents 16 are preferably provided in a first display portion 21A. The first display portion 21A is preferably provided in the middle and/or is not changed by actuation of the switchover means 19, which can be provided on the upper edge.

A second display portion 21B, which is arranged in particular on one side of the display portion 21A, can have the configuration displays 20. In this case, these are schematic illustrations of the display portion 21A having highlighted virtual positions 17 and/or descriptions of the receptacle unit equivalents 16 or pipetting unit equivalents 18 arranged at the respective emphasized virtual positions 17.

Furthermore, in a third display portion 21C, which can be provided in particular on a side of the display portion 21A facing away from the display portion 21B, a configuration menu can be provided for setting different parameters, functions, and/or for selecting one or more of the receptacle unit equivalents 16 and/or pipetting unit equivalents 18. In the setup mode, different pipetting unit equivalents 18 and/or receptacle unit equivalents 16 are preferably selectable in the display portion 21C, whereby they can be assigned to the virtual positions 17.

Separate configuration interfaces 15A can alternatively or additionally also be provided for the individual modes of the configuration interface 15A, wherein preferably the switchover means 19 and/or the display portion 21A are each taken over at least substantially identically in the respective configuration interfaces 15A.

In a programming mode of the first configuration interface 15A, which can be activatable via the switchover means 19, already selected or configured method steps or configurations can be displayable in the second display portion 21B, in particular in a chronological sequence. Commands, method steps, or instructions are preferably selectable in the third display portion 21C.

In an optional simulation mode of the first configuration interface 15A, which can be activatable via the switchover means 19, a configured sequence can be simulated in the configuration interface 15A and/or using the pipetting machine 2, in particular by way of corresponding movements of the pipetting device 4.

In an execution mode, which can be activatable via the switchover means 19, an operating field is preferably provided in the second display portion 21B or third display portion 21C, using which the control unit 1 is controllable such that the pipetting machine 2 is controllable in the previously set up or configured manner by the control unit 1.

Different further configuration interfaces 15B to 15L or a configuration interface 15B to 15L in different variants or having different operating concepts are explained in greater detail hereafter on the basis of FIGS. 3 to 18.

Reference is always made hereafter to different configuration interfaces 15A to 15L, although it can relate to variants thereof. The configuration interfaces 15A to 15L are preferably detail masks or detail illustrations for the individual or detail control of the pipetting machine 2.

The control unit 1 is preferably designed to enable an opening or generating of one or more of the configuration interfaces 15B to 15L, by selecting one or more of the receptacle unit equivalents 16 or pipetting unit equivalents 18 in the configuration interface 15A. In particular, one or more of the receptacle unit equivalents 16 or pipetting unit equivalents 18 is/are selected or marked in the display portion 21A and by operating, in particular actuating of a soft switch of the configuration interface 15A, one or more of the configuration interfaces 15B to 15L is/are generated or displayed subsequently. Other solutions are also possible here, however.

The variants or configuration interfaces 15B to 15L and the related operation or operability of the control unit 1 or of the pipetting machine 2 can also represent or form separate aspects of the invention, which are combinable with one another and are also implementable independently of one another.

A further aspect of the present invention, which is also implementable independently, relates to the combination of the first configuration interface 15A, also referred to hereafter as the master configuration interface 15A, with one or more of the configuration interfaces 15B to 15L, also referred to hereafter as client configuration interfaces 15B to 15L.

It is preferable, that in the (master) configuration interface 15A one or more receptacle unit equivalents 16 and/or one or more pipetting unit equivalents 18 are selectable or will be selected, which then are the basis for one or more of the (client) configuration interfaces 15B to 15L. In particular, the control unit 1 is designed to generate (client) configuration interfaces 15B to 15L from the receptacle unit equivalents 16 or pipetting unit equivalents 18 selected in the (master) configuration interface 15A.

The (client) configuration interfaces 15B to 15L are preferably designed to configure the receiving of liquid and/or the dispensing of liquid by assigning transfer parameters 23. In contrast, the (master) configuration interface 15A is preferably not provided or designed for configuration of individual liquid receiving actions and/or liquid dispensing actions.

The client configuration interfaces 15B to 15L are preferably designed to assign transfer parameters 23 to individuals or groups of the receptacle unit equivalents 16. By way of this assignment of the transfer parameters 23 to the receptacle unit equivalents 16 parameter sets, referred to hereafter as configurations, or means for transferring, storing, displaying, and/or using assignments between receptacle unit equivalents 16 and transfer parameters 23, can preferably be generated in or by means of the (client) configuration interfaces 15B to 15L, in particular in the chronological sequence of the respective assignment.

The configurations which are generated by means of the (client) configuration interfaces 15B to 15L are preferably displayable as or represented by a symbol or another graphic representation in the (master) configuration interface 15A, can be supplemented by further global commands, in particular pause times, tip changes, syringe changes, or the like, and/or are controllable with regard to the sequence of the execution of different configurations. This is preferably performed in the programming mode of the (master) configuration interface 15A. It is preferable for the configurations to be displayed or displayable in the display portion 21B and/or as configuration displays 20. However, other solutions are also possible here.

The hierarchical structure having the (master) configuration interface 15A and the (client) configuration interfaces 15B to 15L hierarchically subordinate thereto offers the advantage of a very comprehensible and structured configurability and control of the pipetting machine 2.

In particular, the (master) configuration interface 15A is designed to display individual or multiple graphic representations of configurations and, by manipulations within the (master) configuration interface 15A, in particular by so-called "drag-and-drop", to change in the sequence, delete, and/or change to accordant or corresponding (client) configuration interfaces 15B to 15L for editing one or more of the configurations, or to generate and display corresponding (client) configuration interfaces 15B to 15L, preferably alternatively to or instead of the (master) configuration interface 15A. It is thus preferable for either the (master) configuration interface 15A or one of the (client) configuration interfaces 15B to 15L to be displayable by the display unit 13, but particularly preferable not multiple ones of the configuration interfaces 15A to 15L at the same time.

A sequence of at least one reception or removal and one dispensing of liquid 6 or a sequence of the assignment of a transfer parameter 23 corresponding to a volume to be removed and the subsequent assignment of a transfer parameter 23 corresponding to a volume to be dispensed is preferably referred to as a transfer. A configuration preferably has at least one or precisely one such transfer, in particular restricted to transfers between the or within the receptacle unit equivalents 16 or pipetting unit equivalents 18 previously selected in the (master) configuration interface 15A.

Transfers are preferably configurable by the (client) configuration interfaces 15B to 15L, but particularly preferable not or not directly by the (master) configuration interface 15A. In conjunction with FIGS. 3 to 18, (client) configuration interfaces 15B to 15L are presented hereafter, which are preferably designed for the configuration of one or more transfers or on the basis of which transfers are described, in particular by a chronological sequence of the steps, which are described hereafter in conjunction with the side identified with 1. and the side identified with 2. These steps, procedures, and the like are alternatively or additionally, however, also implementable individually and combinable with one another.

Figure 3:
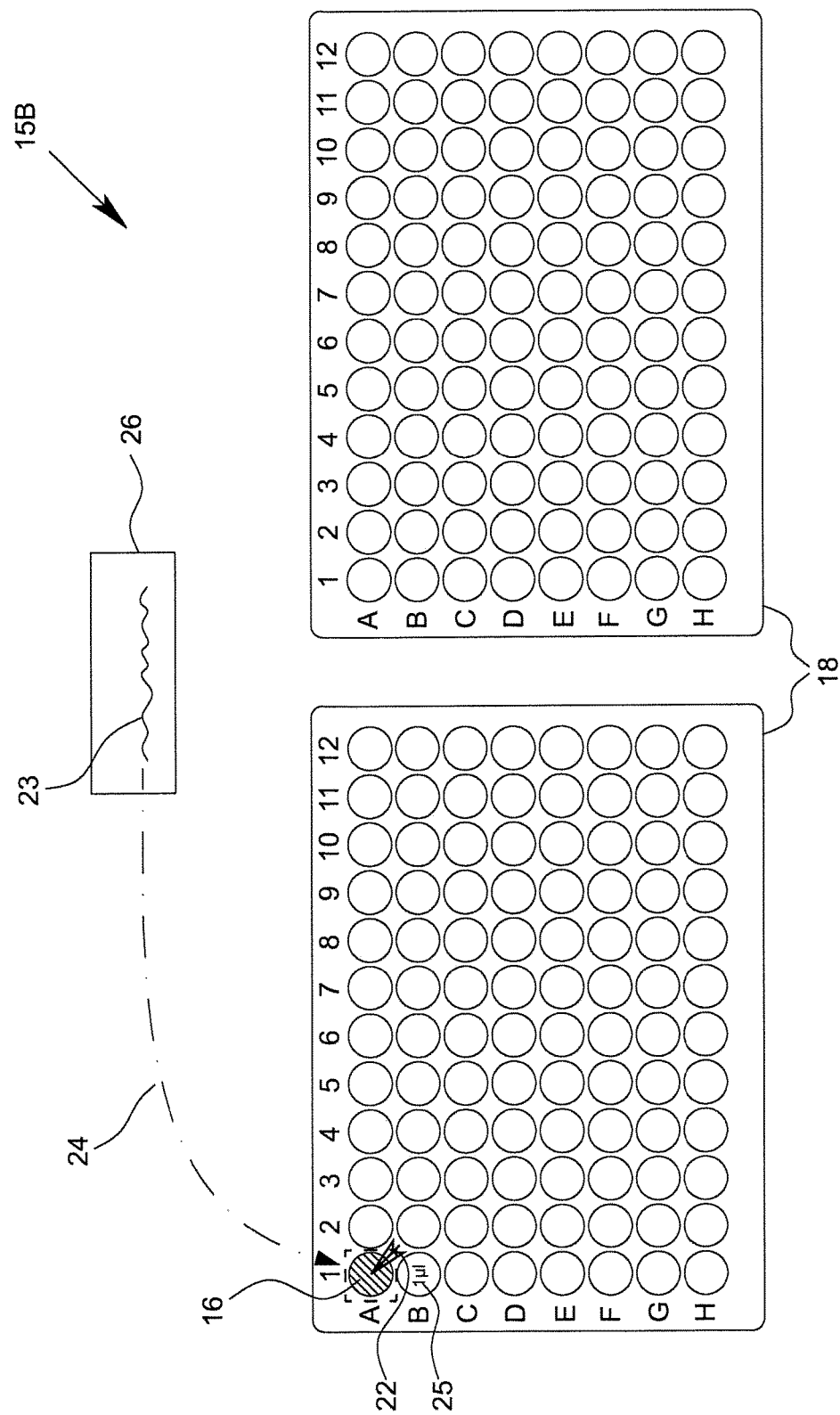
FIG. 3 shows a schematic illustration of a second configuration interface of the proposed control unit.

FIG. 3 shows a schematic illustration of a second configuration interface 15B of the proposed control unit 1, in which two pipetting unit equivalents 18 are provided with a variety of receptacle unit equivalents 16 as examples. The receptacle unit equivalents 16 are arranged at least substantially in a grid or in another manner systematically within the pipetting unit equivalents 18. The receptacle unit equivalents 16 are preferably each arranged in rows and columns like a grid, wherein the rows or columns are each identified such that each individual of the receptacle unit equivalents 16 can be addressed or identified in the manner of coordinates by specifying a row and a column.

Two different or identical pipetting unit equivalents 18 are arranged adjacent to one another in the configuration interface 15B from FIG. 3. In derogation thereof it is also possible, however, that only one pipetting unit equivalent 18, more than two pipetting unit equivalents 18, or one or more receptacle unit equivalents 16 are also provided independently of pipetting unit equivalents 18, preferably corresponding to the occupation of one or more virtual positions 17.

In particular, it is possible that a specific pipetting unit equivalent 18 is provided two or more times in the configuration interface 15B, in particular adjacent to one another, to configure transfers between receptacle unit equivalents 16 of the same pipetting unit equivalent 18 in a comprehensible manner.

One or more receptacle unit equivalents 16 is/are selectable in the configuration interface 15B, in particular using a selection tool 22, for example a cursor.

By selecting the graphic receptacle unit equivalent(s) 16, preferably at least one transfer parameter 23 can be assigned thereto, indicated in FIG. 3 by the arrow 24. The arrow 24 is only used for explanation and is not part of the configuration interface 15B.

The control unit 1 can have a database, in which an associated transfer parameter 23 can be saved or stored for the different receptacle unit equivalents 16, in particular by the selection or assignment. The database can be a table or another data structure.

Preferably, each receptacle unit equivalent 16 is alternatively or additionally assigned to an actual volume parameter 25 representing a liquid volume, which is already contained in the respective receptacle unit 5, which corresponds to the respective display unit equivalent 16, and/or is to be present as a result after carrying out one or more pipetting steps or transfers. The actual volume parameter 25 can be assigned in the configuration interface 15B to the respective receptacle unit equivalent 16, in particular can be displayed or displayable in conjunction herewith or within the respective graphic receptacle unit equivalent 16.

The transfer parameter 23 preferably corresponds to a transfer volume, i.e., to a volume of the liquid 6, which is to be removed from the respective receptacle unit equivalent 16 or dispensed therein.

The control unit 1 is preferably designed to generate control commands, which correspond to the transfer parameters 23, in particular in consideration of the specification or in the sequence thereof, for controlling the pipetting machine 2 and to transmit them, preferably via the data interface 9, to the pipetting machine 2. In this way, the control unit 1 causes a control of the pipetting machine 2 such that the receiving of the transfer volume from or the dispensing of the transfer volume into the respective receptacle unit 5 is brought about. This is performed in particular by activating one or more of the actuators 3A, 3B, 3C of the pipetting machine 2.

According to one aspect of the present invention, which is also implementable independently, it is provided that the control unit 1 or the configuration interface 15B is designed so that the transfer parameter 23 is settable or pre-definable in or using the configuration interface 15B. In particular, the configuration interface 15B has an input mask 26 or a menu, a selection field, or the like, in which the transfer parameter 23 can be input, selected, changed, or predefined in another manner, in particular by means of the keyboard 11.

The transfer parameter 23 is preferably settable on the same configuration interface 15B, on which individual receptacle unit equivalents 16 are also selectable and the transfer parameter 23 is assignable thereto. This has proven to be particularly advantageous for rapid configuration and comprehensible operation of the pipetting machine 2 using the control unit 1.

The transfer parameter 23 particularly preferable is or corresponds to the transfer volume, i.e., a liquid volume of the liquid 6, which is to be received by the pipetting device 4 using the pipette tip(s) 7 or is to be dispensed thereby.

Alternatively or additionally, the transfer parameter 23 can also be, have, or correspond to a transfer material quantity, in particular in moles, a transfer tool, in particular a single-channel or multichannel pipetting device 4, a transfer pattern, and/or a transfer or target concentration. The transfer parameter particularly preferably corresponds, however, in each case to one transfer volume, which can be determined or calculated from the transfer material quantity, the transfer or the target concentration.

Figure 4:
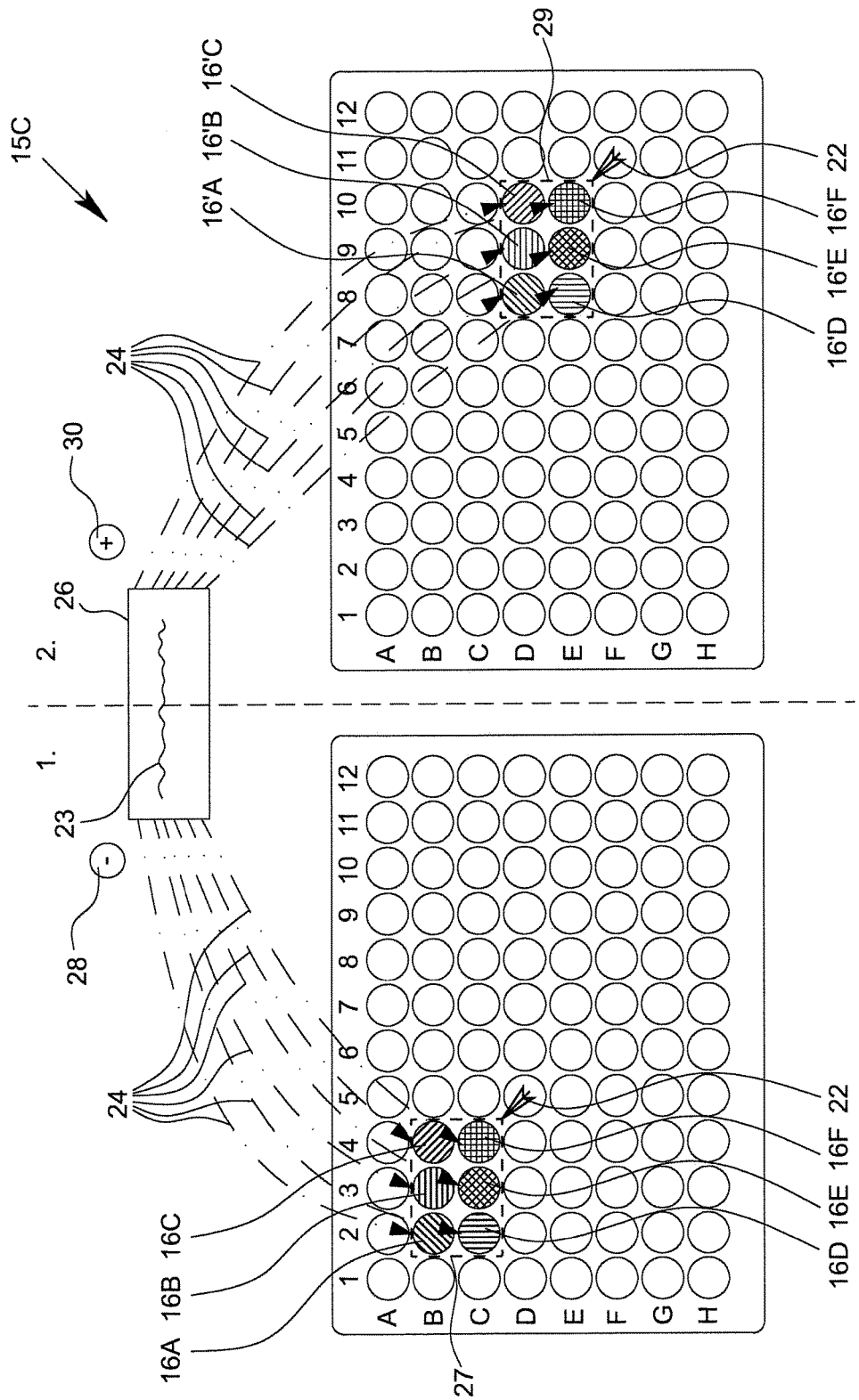
FIG. 4 shows a schematic illustration of a third configuration interface of the proposed control unit.

FIG. 4 shows a schematic illustration of a third configuration interface 15C of the proposed control unit 1.

For fundamental aspects, in particular relating to the assignment of the transfer parameter 23, reference is explicitly made at this point to the explanations in conjunction with FIG. 3. Therefore, further special details of more complex control procedures are only discussed hereafter, preferably wherein the characteristics and features described in conjunction with FIG. 3 are used as the basis or are accordingly applicable. This applies accordingly for the further configuration interfaces 15D to 15L, which are explained in conjunction with FIGS. 5 to 18.

The configuration interface 15C from FIG. 4 is divided, for reasons of better comprehension, using a dashed line into a first and a second portion, wherein this dashed line and the numbers 1 and 2 are not part of the configuration interface 15C, but are there rather only to represent a preferred chronological sequence. In a corresponding manner, the arrows 24 are also only used for explanation, but are preferably not displayed in the respective configuration interface 15 and are not part thereof, however.

A receptacle unit equivalent 16 or a first group 27, which is emphasized here by dashed lines, of receptacle unit equivalents 16A to 16F is preferably selected on the first side in the configuration interface 15C. By selecting the receptacle unit equivalents 16A to 16F, the transfer parameter(s) 23 is/are preferably assigned to these receptacle unit equivalents 16A to 16F, as indicated by the arrows 24.

The respective transfer parameter 23, which is assigned in each case in this first step, is preferably a transfer parameter 23 which corresponds to one or more transfer volumes to be removed, which is indicated in the configuration interface 15C using the minus symbol 28, which is only used for purposes of explanation and is preferably not part of the configuration interface 15C and is not displayable by means of the control unit 1.

After selection of a first receptacle unit equivalent 16A to 16F or multiple first receptacle unit equivalents 16A to 16F as a first group 27 on the first side, thereafter, a second selection of a second receptacle unit equivalent 16'A to 16'F or a selection of a second group 29 of second receptacle unit equivalents 16'A to 16'F can be performed on the second side. Transfer parameters 23 corresponding to one or more transfer volumes to be dispensed are preferably assigned by this selection to the respective second receptacle unit equivalents 16'A to 16'F. In the configuration interface 15C, this chronological sequence is symbolized by the middle dashed line and the identification with 1. and 2.

It is preferable that, during a first selection, which is performed on the first side, of a first receptacle unit equivalent 16A to 16F or a first group 27 of first receptacle unit equivalents 16A to 16F, a transfer parameter 23 corresponding to a transfer volume to be removed is assigned automatically to each selected first receptacle unit equivalent 16A to 16F. If this first selection is followed by a second selection, which is performed on the second side, of a second receptacle unit equivalent 16'A to 16'F or a group 29 of second receptacle unit equivalents 16'A to 16'F, it is preferable if a transfer parameter 23 corresponding to a transfer volume to be dispensed is automatically assigned to each selected second receptacle unit equivalent 16'A to 16'F.

The first receptacle unit equivalents 16A to 16F, to which a transfer parameter 23 is assigned, which corresponds to a transfer volume to be removed, and which are also indicated using the minus symbol 28, are also referred to as source receptacle unit equivalents. Second receptacle unit equivalents 16'A to 16'F, to which a transfer parameter 23 is assigned and which correspond to a transfer volume to be dispensed, are preferably also referred to as target receptacle unit equivalents. A selection of receptacle unit equivalents 16 on the first side thus preferably automatically results in the definition of source receptacle unit equivalents 16A to 16F, while a selection of receptacle unit equivalents 16 on the second side results in the definition of target receptacle unit equivalents 16'A to 16'F.

Upon the selection of a group 27 of first receptacle unit equivalents 16A to 16F on the first side and the following selection of a group 29 of second receptacle unit equivalents 16'A to 16'F on the second side, a paired 1:1 assignment is preferably performed automatically. If a multichannel pipetting device 4 is used, corresponding to the groups 27, 29, this 1:1 assignment is achieved or enabled automatically by separate pipette tips 7. Upon selection of groups 27, 29, which do not correspond to a multichannel pipetting device 4, after selection of the groups 27 and 29, assignments or transfer operations are automatically split up, so that by the controller single transfers are performed or individual selections, which each alternate between the group 27 of first receptacle unit equivalents 16A to 16F and the group 29 of second receptacle unit equivalents 16'A to 16'F, are assumed or it is achieved in another manner that in each case a paired assignment is produced.

In the illustrated example, the control unit 1 is designed and set up to control, in dependence on the number of the pipette tips 7 of the respective selected pipetting device 4, the pipetting machine 2 after selection of two groups 27, 29 such that in successive operations, liquid 6 is gradually transferred from the receptacle units 5 corresponding to the first receptacle unit equivalents 16A to 16F in each case into the receptacle units 5 corresponding to the second receptacle unit equivalents 16'A to 16'F.

In the configuration interface 15C, receptacle unit equivalents 16 assigned to one another or corresponding to one another are preferably associated with one another or identified identical. In the illustrated example, receptacle unit equivalents 16 associated with or corresponding to one another have the same shading. Alternatively or additionally, however, the same or identical colors or other markings can also be used.

Figure 5:
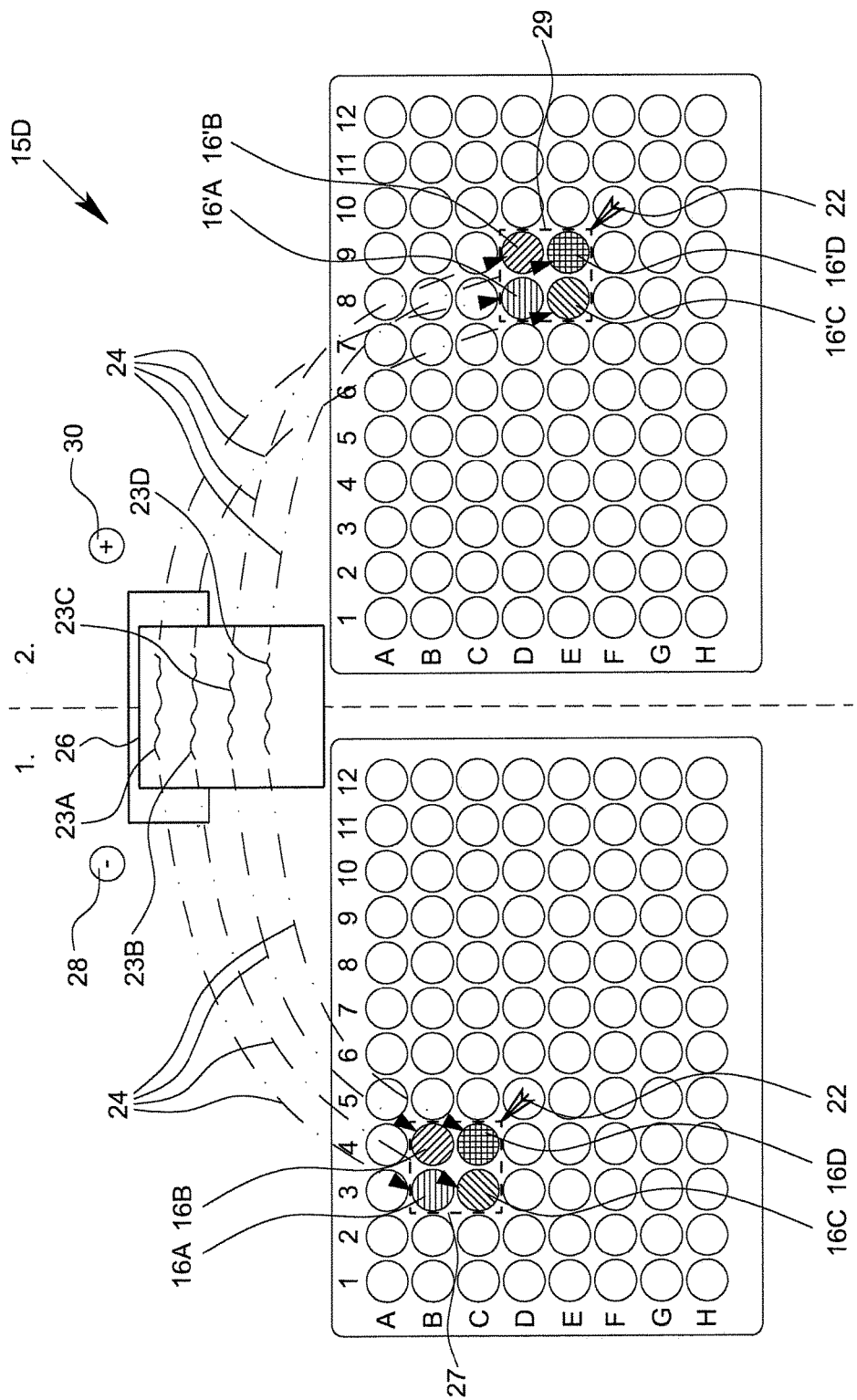
FIG. 5 shows a schematic illustration of a fourth configuration interface of the proposed control unit.

FIG. 5 shows a schematic illustration of a fourth configuration interface 15D, with which or in which preferably one or more volume difference(s) or multiple volumes is/are pre-definable as transfer parameter 23 or for ascertaining the respective transfer parameter 23.

A volume difference or a transfer parameter 23 corresponding to a volume difference can preferably be specified, determined, or selected, in particular in an input mask 26. By selecting multiple receptacle unit equivalents 16A to 16D or a group 27 on the first side, the respective transfer parameter 23, which is assigned or is to be assigned, of a next receptacle unit equivalent 16 of the group 27 is preferably selected automatically corresponding to a transfer volume, which deviates by the volume difference from a transfer volume to which the transfer parameter 23 corresponds, which has previously been assigned to a receptacle unit equivalent 16.

In the illustrated example, multiple volume differences or volumes are predefined as transfer parameters 23A to 23D. The control unit 1 or the configuration interface 15D is preferably designed and set up so that, upon selection of one group 27 of receptacle unit equivalents 16A to 16D, the transfer parameters 23A to 23D are assigned in each case. The transfer parameters 23A to 23D can be specifiable or specified as absolute values, in particular in the form of a list or the like, or as volume differences. If volume differences are predefined or specified, a transfer parameter 23A to 23D, which corresponds to a transfer volume, which deviates by the respective volume difference in comparison to the transfer volume to which a transfer parameter 23 of the previous receptacle unit equivalent 16A to 16D corresponds, is automatically assigned to the receptacle unit equivalent 16A to 16D following a previous receptacle unit equivalent 16A to 16D.

In the illustrated example according to FIG. 5, a first transfer parameter 23A, which preferably corresponds to a predefined transfer volume and/or the value of the volume difference, is assigned to a first receptacle unit equivalent 16A. Subsequently, a second transfer parameter 23B is assigned to a second receptacle unit equivalent 16B, the second transfer parameter 23B corresponding to another absolute transfer volume or to a transfer volume which deviates by a specified volume difference, preferably is greater than the transfer volume to which the transfer parameter 23A of the receptacle unit equivalent 16A corresponds.

Upon the specification of volume differences, it is possible to specify a starting value, which is assigned to the first receptacle unit equivalent 16A of a group 27 and to specify a volume difference, wherein the second assigned transfer parameter 23B corresponds to a transfer volume, which deviates by the volume difference from the starting value, and wherein with each further assignment of a further transfer parameter 23C, 23D, the further transfer parameter 23C, 23D corresponds in each case to a transfer volume which is changed (once again in each case) by the specified volume difference.

Transfer parameters 23, corresponding to transfer volumes which deviate from one another by volume differences or correspond to specified volumes, are preferably accordingly assigned, beginning from the top left, from left to right and row-by-row from top to bottom. However, other solutions are also possible here.

As already explained in conjunction with FIG. 4, upon selection of a second receptacle unit equivalent 16'A to 16'D on the second side, transfer parameters 23A to 23D are assigned in a corresponding manner. A 1:1 assignment of the receptacle unit equivalents 16A to 16D to the receptacle unit equivalents 16'A to 16'D is preferably performed, wherein a division into individual transfer operations can be performed for the control of the pipetting machine 2, as explained as an example in conjunction with FIG. 4.

The volume differences, the starting value, and the volume difference and/or the volumes can be entered or are enterable as transfer parameters 23A to 23D or for forming transfer parameters 23 in a list, table, or in particular a self-expanding input mask 26 or a context menu.

Figure 6:
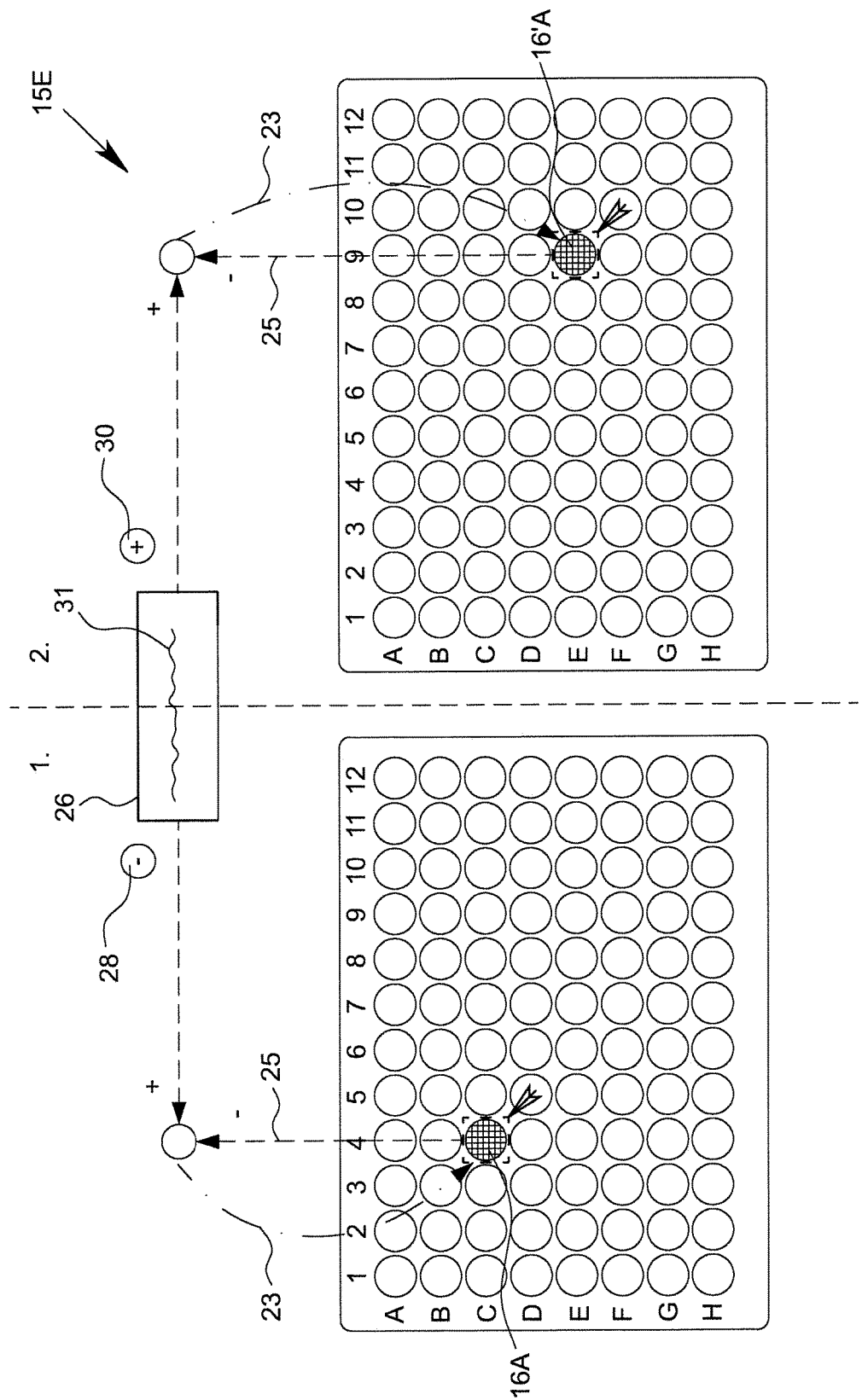
FIG. 6 shows a schematic illustration of a fifth configuration interface of the proposed control unit.

FIG. 6 shows a schematic illustration of a fifth configuration interface 15E. A target volume 31 can preferably be input on or in the configuration interface 15E, in particular in an input mask 26. The control unit 1 is preferably designed, by selecting a receptacle unit equivalent 16A, to assign a transfer parameter thereto, which corresponds to a transfer volume, which corresponds to a difference between the target volume 31 and an actual volume, which is already assigned to the receptacle unit equivalent 16A or another receptacle unit equivalent 16, 16'.

The actual volume is preferably represented by the actual volume parameter 25. In particular, upon selection of a receptacle unit equivalent 16A, the actual volume parameter 25 of this or another receptacle unit equivalent 16, 16' is subtracted from a parameter corresponding to the target volume 31, and a transfer parameter 23 corresponding to the result is assigned to the receptacle unit equivalent 16A. In this way, the receptacle unit 5 corresponding to the receptacle unit equivalent 16A is filled up or emptied or can be filled up or emptied to the target volume 31 upon control of the pipetting machine 2 using the control unit 1.

The target volume 31 can thus relate to a source receptacle unit equivalent 16 or to a target receptacle unit equivalent 16'. In the first case, a corresponding amount of liquid 6 is removed from the receptacle unit 5 corresponding to the source receptacle unit equivalent 16. In the second case, a corresponding amount of liquid 6 is added to the receptacle unit 5 corresponding to the target receptacle unit equivalent 16'.

In FIG. 6, corresponding operations are illustrated using arrows, which are preferably not part of the configuration interface 15E and are only used for explanation. As above, in FIG. 6 the configuration interface 15E is also divided into two parts by a dashed line, which is only used for explanation, specifically into a portion identified with 1. and a portion identified with 2., which preferably corresponds to a chronological sequence of selections. On the side which is identified with 1, a first selection of the receptacle unit equivalent 16A is thus explained, and subsequently a second selection of another receptacle unit equivalent 16'A is explained on the basis of the side identified with 2.

The receptacle unit equivalent 16'A is preferably a target receptacle unit equivalent. As already described in conjunction with the receptacle unit equivalent 16A, which is preferably a source receptacle unit equivalent, the transfer parameter 23 or the transfer volume corresponding thereto can be determined or calculated in a corresponding manner, preferably by the control unit 1.

It is not absolutely necessary for the transfer parameter 23 to be determined and assigned in a way such that the target volume 31 is achievable on both sides, or both on the side of the source receptacle unit equivalent 16A and also on the side of the target receptacle unit equivalent 16'A. For example, on the source side, the entire available volume of the respective pipette tip 7 can be exhausted and one or more receptacle unit equivalents 16 can be brought in the described manner to the target volume 31. Alternatively or additionally, transfer parameter(s) 23 for source receptacle unit equivalents 16A can be determined, in particular also independently of the respective target receptacle unit equivalent 16'A, such that during control of the pipetting machine, enough liquid 6 is removed that the target volume 31 is achieved or is achievable. These aspects are also combinable with one another, however, as shown in FIG. 6.

Furthermore, it is possible that one or more groups 27, 29 of receptacle unit equivalents 16, 16' are selected and in each case a transfer parameter 23 is determined in a corresponding manner for the individual receptacle unit equivalent 16A, 16'A and assigned in each case to the receptacle unit equivalent 16A, 16'A, in particular with a paired 1:1 assignment. Furthermore, it is possible that, in a corresponding manner as was described in conjunction with FIG. 5 or configuration interface 15B, multiple target volumes 31 are specified and the determination of the respective transfer parameters 23 is based on these different target volumes 31 or target volumes 31 changed in each case by means of the volume difference.

Figure 7:
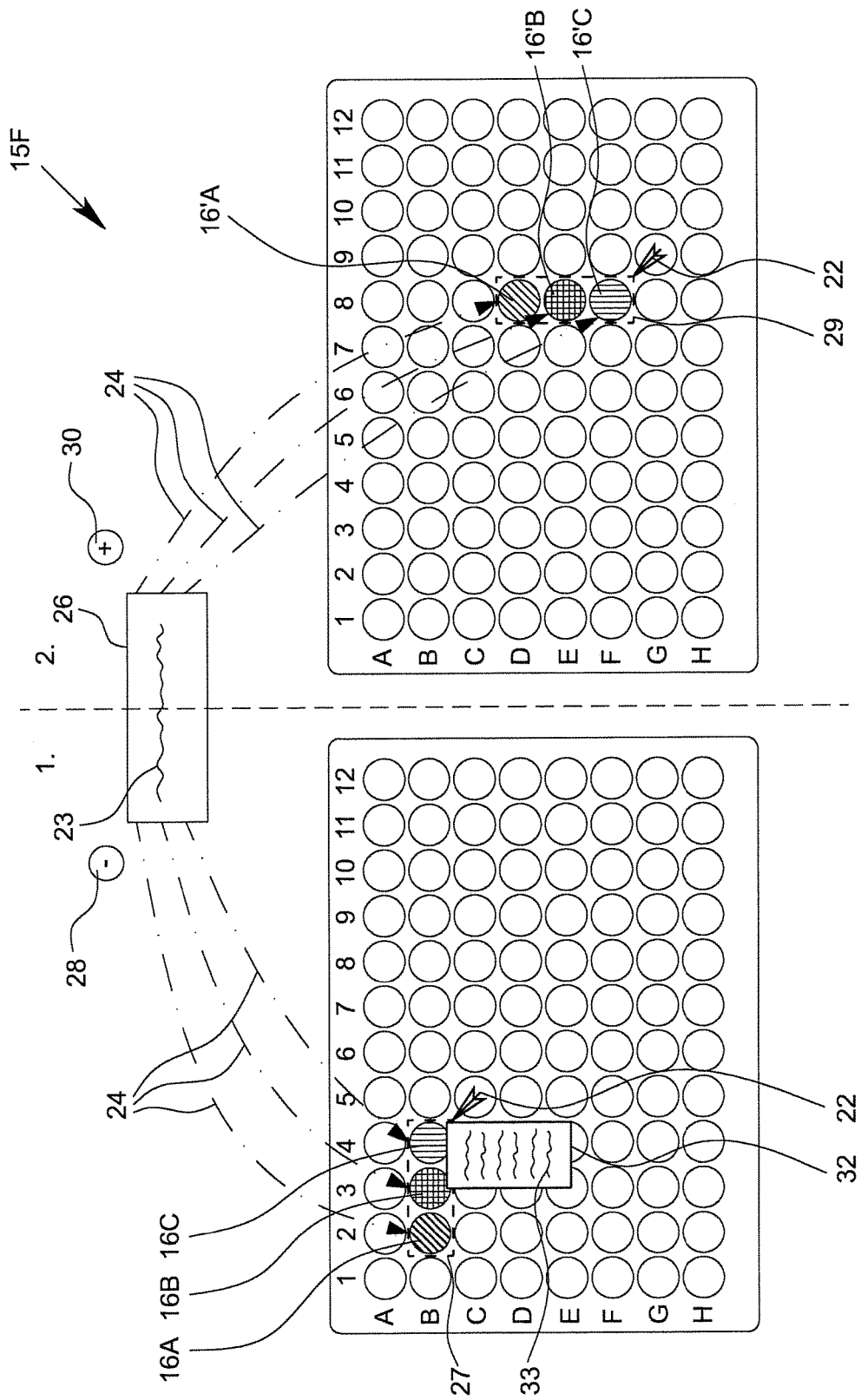
FIG. 7 shows a schematic illustration of a sixth configuration interface of the proposed control unit.

FIG. 7 shows a schematic illustration of a sixth configuration interface 15F of the proposed control unit 1.

In the present configuration interface 15F, multiple receptacle unit equivalents 16A to 16C are preferably selectable successively or simultaneously as a first group 27 on the first side as source receptacle unit equivalents 16, wherein preferably transfer parameters 23 can be assigned corresponding to the manner described in conjunction with FIGS. 3 to 18.

A context menu 32 can preferably be generated or activated in the configuration interface 15F, in particular by selection or alternative selection of the first group 27 or the source receptacle unit equivalents 16A to 16C. The context menu 32 preferably has one or more options 33 for the virtual modification of the structure or arrangement and/or number of the selected source receptacle unit equivalents 16A to 16C of the group 27 for a following or further selection of target receptacle units 16'A to 16'C. The modification is virtual in that the selected source receptacle unit equivalents 16A to 16C themselves are not modified, but rather a transfer pattern (i.e., a graphic representation) is generated and this is modified.

By selection of the source receptacle unit equivalents 16A to 16C, a graphic representation or marking of the selected source receptacle unit equivalents 16A to 16C is displayed. The graphic representation or marking can then be changed with respect to the number and arrangement of the receptacle unit equivalents by means of the options 33 of the context menu 32. Finally, on the basis of the graphic representation or marking, multiple target receptacle unit equivalents 16'A to 16'C can be selected simultaneously (i.e., synchronously) as a second group 29 on the second side. By way of the selection, the selected source receptacle unit equivalents 16A to 16C are simultaneously assigned to the target receptacle unit equivalents 16'A to 16'C.

The selected source receptacle unit equivalents 16A to 16C are therefore assignable simultaneously (all at once) to multiple target receptacle unit equivalents 16'A to 16'C such that the arrangement and/or number of the assigned target receptacle unit equivalents 16'A to 16'C differs from the arrangement and/or number of the selected source receptacle unit equivalents 16A to 16C. Transfer parameters 23 are thus assigned to the selected source receptacle unit equivalents 16A to 16C and their assigned target receptacle unit equivalents 16'A to 16'C, such that in each case the corresponding transfer volume is transferable from the receptacle units 5 corresponding to the selected source receptacle unit equivalents 16'A to 16'C into the receptacle units 5 corresponding to the assigned target receptacle unit equivalents 16'A to 16'C.

As is apparent in FIG. 7, the assigned target receptacle unit equivalents 16'A to 16'C are displayable in the same configuration interface 15F as the selected source receptacle unit equivalents 16A to 16C.

Using the context menu 32 or also in another manner, which is preferably provided in the configuration interface 15F, it is preferably selectable or selected as an option 33 that the arrangement of the target receptacle unit equivalents 16'A to 16'C corresponds to a reflection, rotation, row-by-row or column-by-column exchange, and/or row-by-row or column-by-column shift of the arrangement of the selected source receptacle unit equivalents 16A to 16C. In particular, after selection of the group 27 and the option 33, a marking, which is changed in the arrangement, of the source receptacle unit equivalents 16A to 16C is indicated, by which a second group 29 of target receptacle unit equivalents 16'A to 16'C is selectable.

In the illustrated example, a marking, which corresponds to the first group 27 and which has been changed in the arrangement, is emphasized in the region of the selection tool 22 and can be assigned by activation of the selection tool 22 by means of the input unit 10 to a corresponding group 29 of target receptacle unit equivalents 16'A to 16'C. In this way, as indicated by arrows 24, corresponding transfer parameters 23 are preferably assigned to the target receptacle unit equivalents 16'A to 16'C.

The control unit 1 is preferably designed to control the pipetting machine 2 such that, either using a multichannel pipetting device 4 or, decomposed into multiple transfer operations, using a single-channel pipetting device 4, a 1:1 volume transfer is performed between the individual receptacle units 5, which correspond, on the one hand, to the group 27 or the source receptacle unit equivalents 16A to 16C and, on the other hand, to the group 29 or the target receptacle unit equivalents 16'A to 16'C. Thus, in particular liquid 6 is received from the receptacle unit 5, which corresponds to the source receptacle unit equivalent 16A, and, after corresponding movement of the pipetting device 4, is dispensed into the receptacle unit 5 corresponding to the target receptacle unit equivalent 16'A. A corresponding operation then follows in conjunction with the source receptacle unit equivalent 16B and the target receptacle unit equivalent 16'B and, preferably subsequently, with the source receptacle unit equivalent 16C and the target receptacle unit equivalent 16'C. In this manner, liquid 6 is transferable by means of the control unit 1 and the pipetting machine 2 such that neighboring conditions and alignments of liquids 6 are systematically changeable in the respective receptacle units 5.

Figure 8:
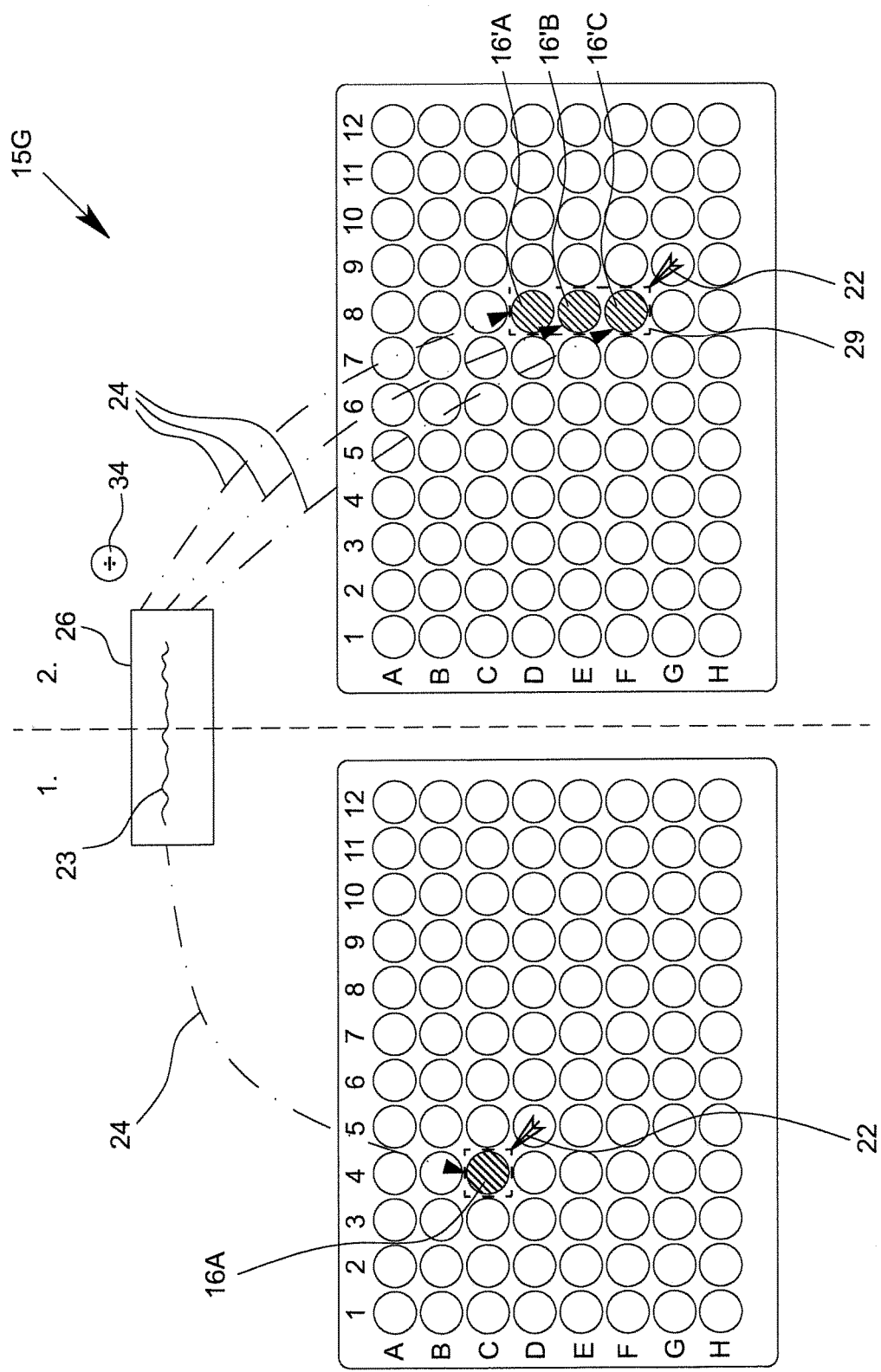
FIG. 8 shows a schematic illustration of a seventh configuration interface of the proposed control unit.

FIG. 8 shows a schematic illustration of a seventh configuration interface 15G, in which, after selection of a source receptacle unit equivalent 16A, multiple target receptacle unit equivalents 16'A to 16'C or a group 29 corresponding thereto is/are selectable, whereby transfer parameters 23 are assigned or are assignable such that the transfer volume to be received from the receptacle unit 5 corresponding to the source receptacle unit equivalent 16A is divided among the receptacle units 5 corresponding to the target receptacle unit equivalents 16'A to 16'C. This is indicated in FIG. 8 by the division symbol 34.

Figure 9:
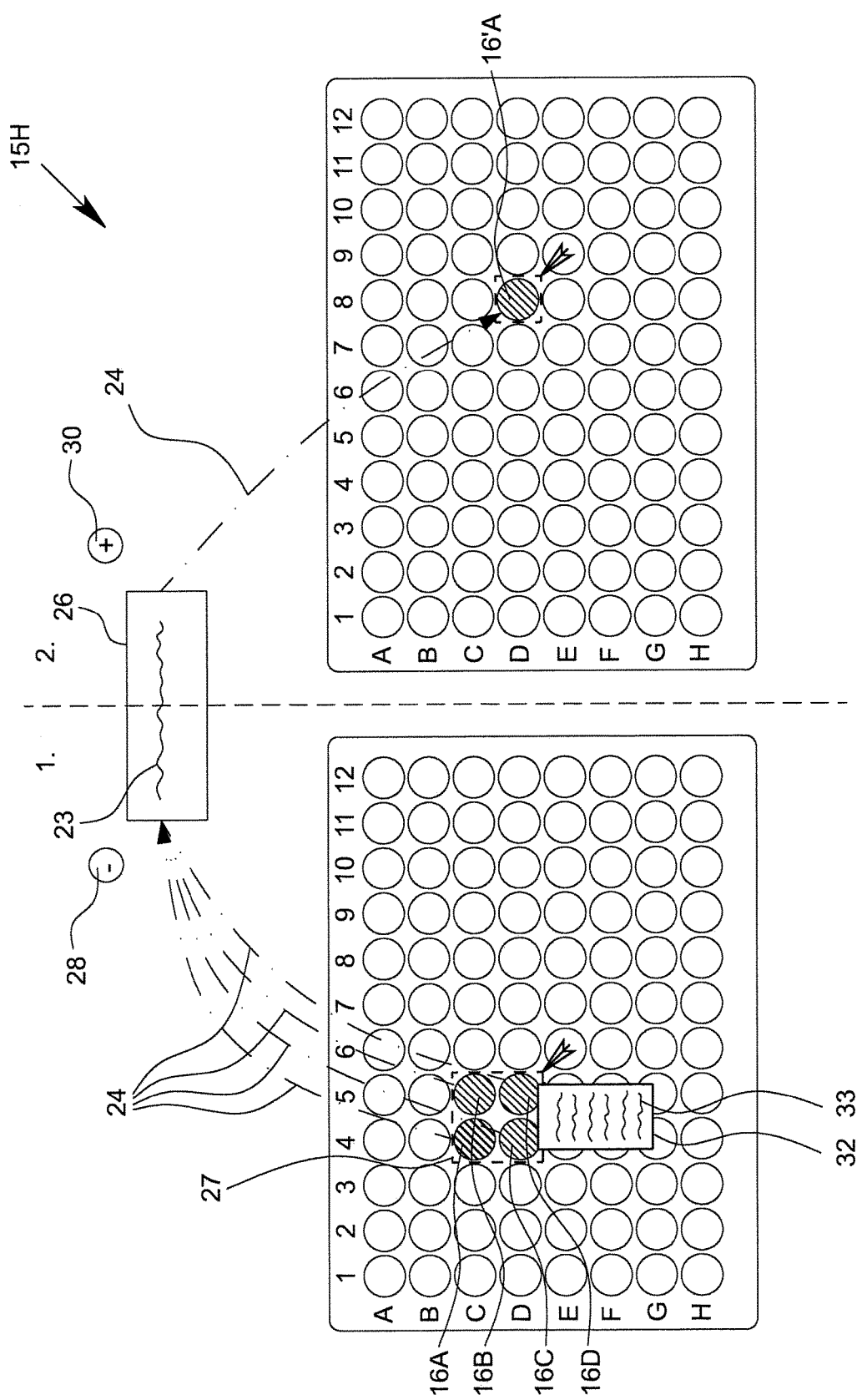
FIG. 9 shows a schematic illustration of an eighth configuration interface of the proposed control unit.

FIG. 9 shows a schematic illustration of an eighth configuration interface 15H of the proposed control unit 1. In the configuration interface 15H, after selection of multiple source receptacle unit equivalents 16A to 16D (corresponding to group 27), a single target receptacle unit equivalent 16'A is selectable, whereby transfer parameters 23 are assigned or are assignable such that the transfer volumes to be received from the receptacle units 5 corresponding to the source receptacle unit equivalents 16A to 16D are combined in the receptacle unit 5 corresponding to the target receptacle unit equivalent 16'A.

For the activation of the division or combination, as described in conjunction with FIGS. 8 and 9, a context menu 32 can be used, or an option 33 can be selected in another manner in the configuration interface 15G, 15H, with which a corresponding division and/or combination can be activated as described above.

Figure 10:
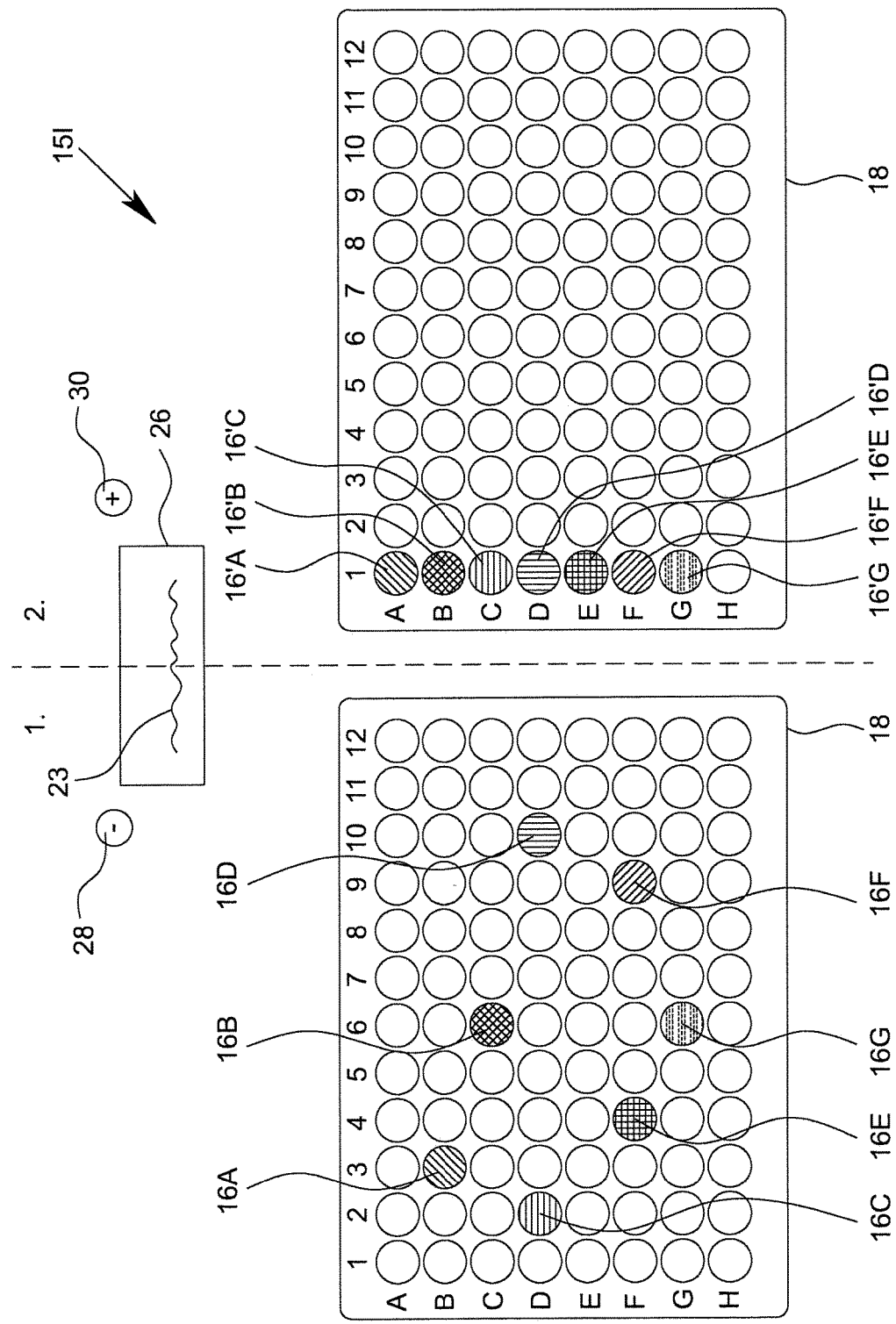
FIG. 10 shows a schematic illustration of a first example of a ninth configuration interface of the proposed control unit.

FIG. 10 shows a schematic illustration of a ninth configuration interface 15I of the proposed control unit 1. In the configuration interface 15I, multiple unbundled source receptacle unit equivalents 16A to 16G are selected and displayed on the first side. In this case, the term "unbundled" is to be understood to mean that on one of the shortest paths (oriented on rows and columns) between at least two receptacle unit equivalents, at least one non-selected receptacle unit equivalent is located, i.e., the selection does not relate to continuously adjacent receptacle unit equivalents.

Using the context menu 32 or also in another manner, which is preferably provided in the configuration interface 15I, it can preferably be selectable or selected as an option 33 that the selected, unbundled source receptacle unit equivalents 16A to 16G are simultaneously assignable to target receptacle unit equivalents 16'A to 16'G on the second side such that the target receptacle unit equivalents 16'A to 16'G are arranged in a bundled manner, preferably in columns. It can preferably be specified in this case in how many columns located adjacent to one another the target receptacle unit equivalents 16'A to 16'G are to be arranged.

In the example illustrated in FIG. 10, the unbundled source receptacle unit equivalents 16A to 16G, which are selected on the first side, are assigned to the target receptacle unit equivalents 16'A to 16'G, which are arranged one under another in column 1 on the second side. Here, "1" was thus selected as the number of columns.

Figure 11:
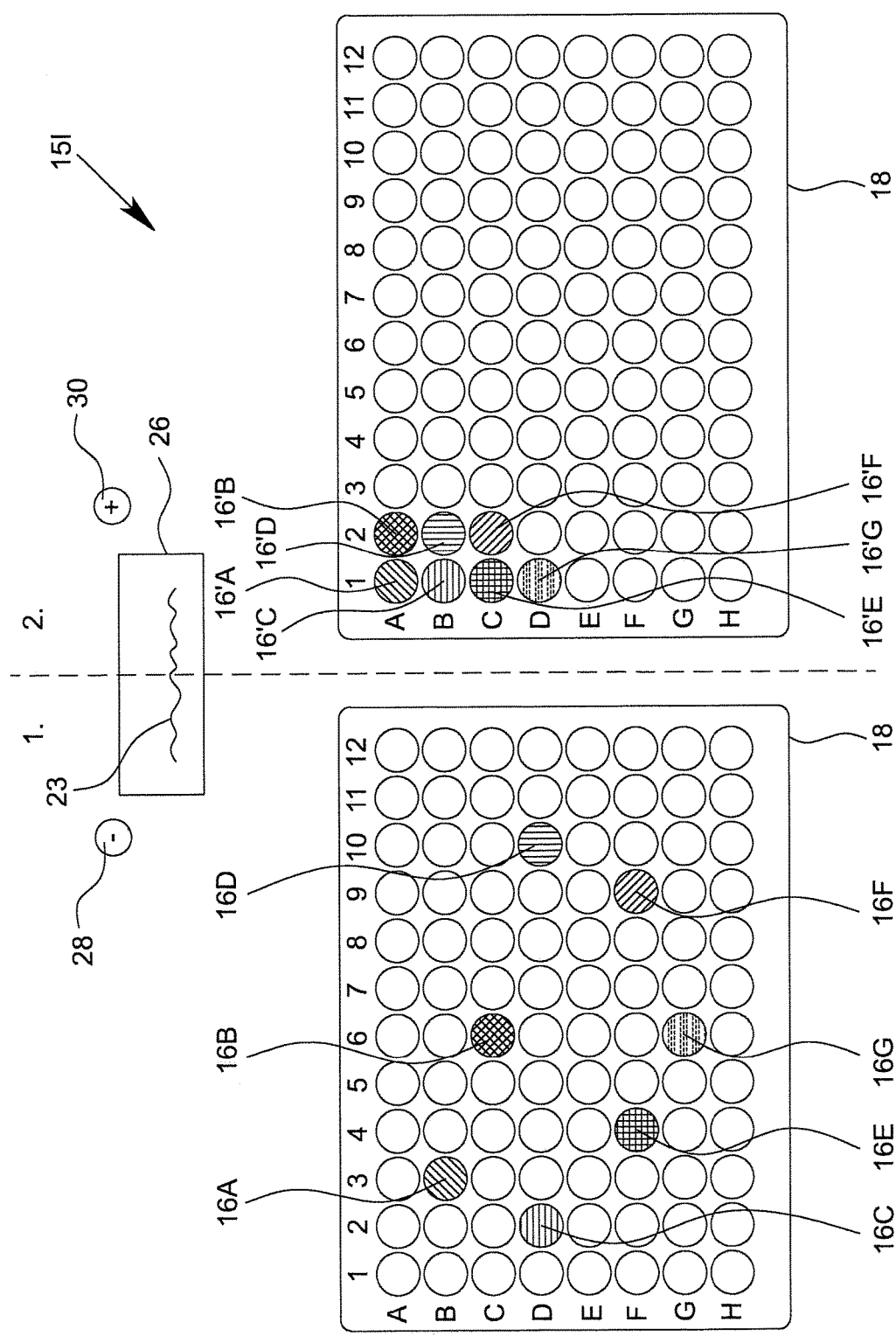
FIG. 11 shows a schematic illustration of a second example of the ninth configuration interface of the proposed control unit.

In the example illustrated in FIG. 11, the unbundled source receptacle unit equivalents 16A to 16G, which are selected on the first side, are assigned to the target receptacle unit equivalents 16'A to 16'G, which are arranged in columns 1 and 2 on the second side. Here, "2" was selected as the number of columns.

Figure 12:
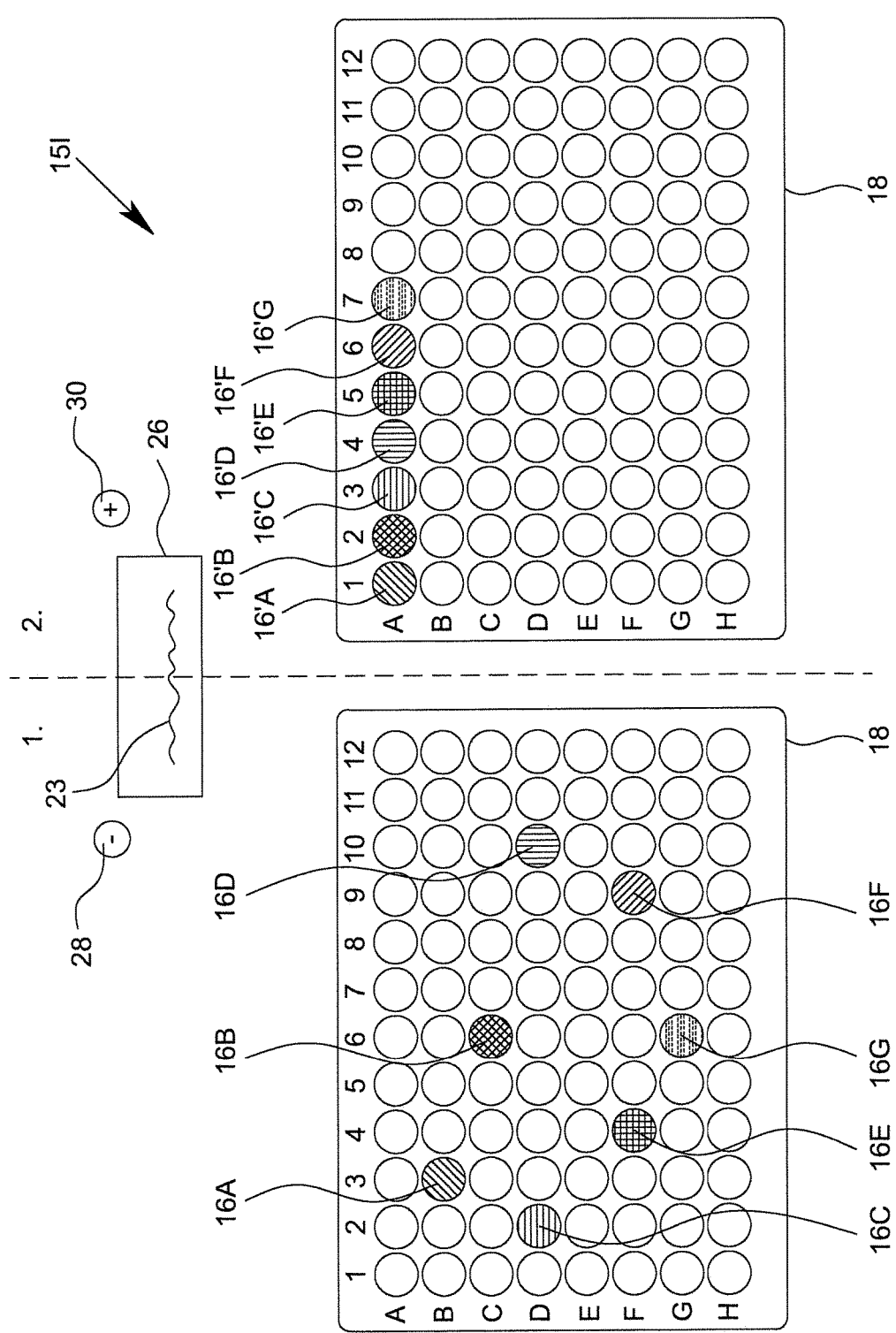
FIG. 12 shows a schematic illustration of a third example of the ninth configuration interface of the proposed control unit.

In the example illustrated in FIG. 12, the unbundled source receptacle unit equivalents 16A to 16G, which are selected on the first side, are assigned to the target receptacle unit equivalents 16'A to 16'G, which are arranged adjacent to one another on the second side in row 1. Here, "7" or more was selected as the number of columns.

Figure 13:
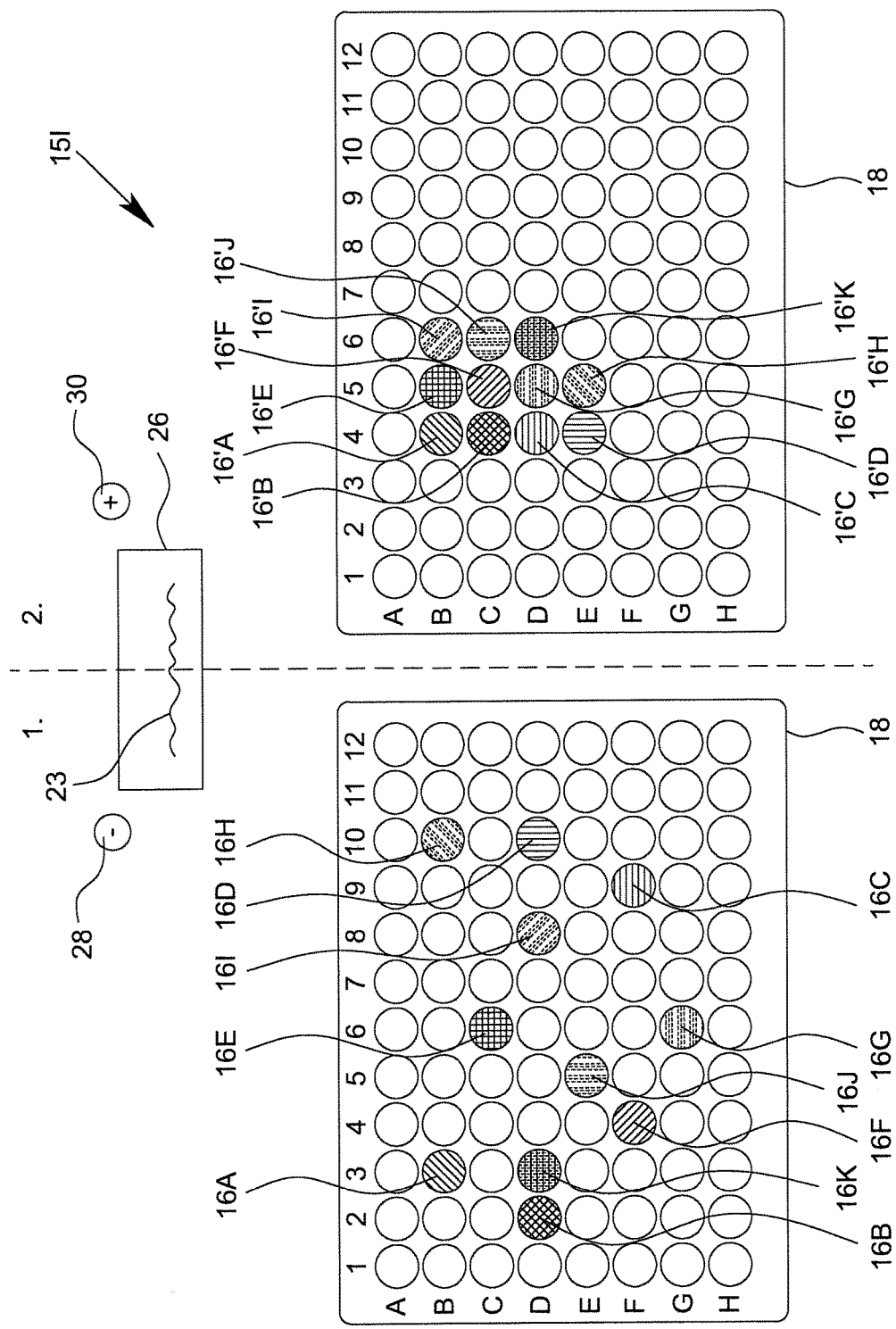
FIG. 13 shows a schematic illustration of a fourth example of the ninth configuration interface of the proposed control unit

In the example illustrated in FIG. 13, the unbundled source receptacle unit equivalents 16A to 16K, which are selected on the first side, are assigned to the target receptacle unit equivalents 16'A to 16'K arranged on the second side in columns 4 to 6. Here, "3" was selected as the number of columns. In addition, the receptacle unit equivalent in row B, column 4 on the second side was selected as the uppermost left target receptacle unit equivalent 16'A.

Figure 14:
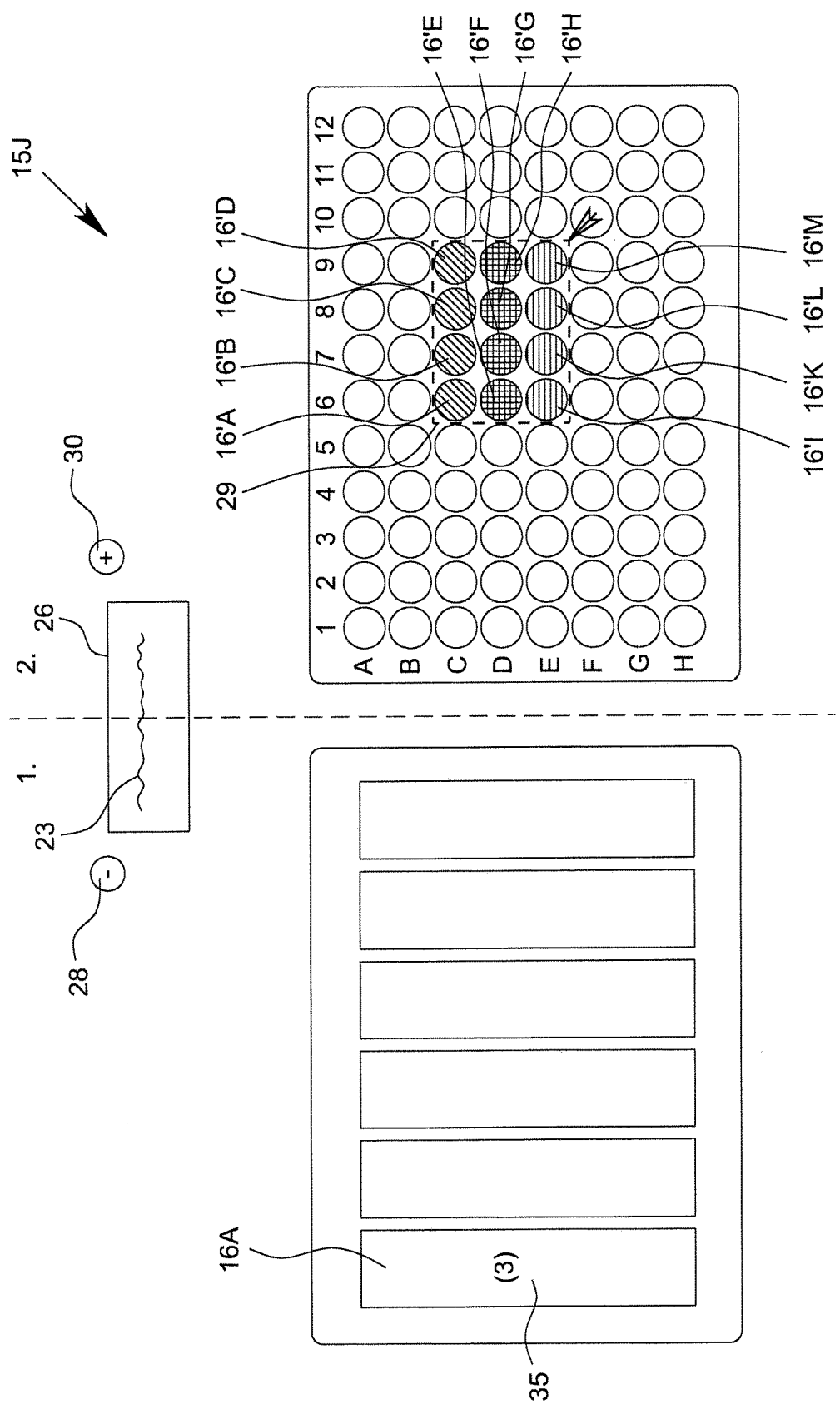
FIG. 14 shows a schematic illustration of a tenth configuration interface of the proposed control unit.

FIG. 14 shows a schematic illustration of a tenth configuration interface 15J of the proposed control unit 1. It is provided here that upon simultaneous selection of multiple receptacle unit equivalents 16'A to 16'M, in particular target receptacle unit equivalents 16'A to 16'M, into the corresponding receptacle units 5 of which liquid 6 is to be dispensed, so that the total liquid quantity to be dispensed exceeds a predefined transfer volume transferable in one step, in particular receptacle volume of the pipetting device 4 or of the pipette tips 7, one further or multiple further transfer parameters 23, which do not exceed the predefined transfer volume, are automatically assigned to the receptacle unit equivalents 16A, 16'A to 16'M, so that a corresponding quantity of liquid 6 is removed step-by-step successively and in an alternating manner from the receptacle unit 5 corresponding to the receptacle unit equivalent 16A and is dispensed at the receptacle units 5 corresponding to the receptacle unit equivalents 16'A to 16'M.

For this purpose, the previously selected (source) receptacle unit equivalent 16A is preferably provided in the configuration interface 15J with a graphic indicator 35 corresponding to the number of automatic further assignments. In the illustrated example, the number of the removal operations is indicated using the indicator 35, in particular by means of a number.

Alternatively or additionally, the target receptacle unit equivalents 16'A to 16'M, into the corresponding receptacle units 5 of which liquid 6 is dispensed in a common transfer step, are marked graphically identical and in comparison to the target receptacle unit equivalents 16'A to 16'M, which participate in another transfer step, are marked graphically differentiated, in particular in a different color. In the illustrated example, this is performed by different shading.

Figure 15:
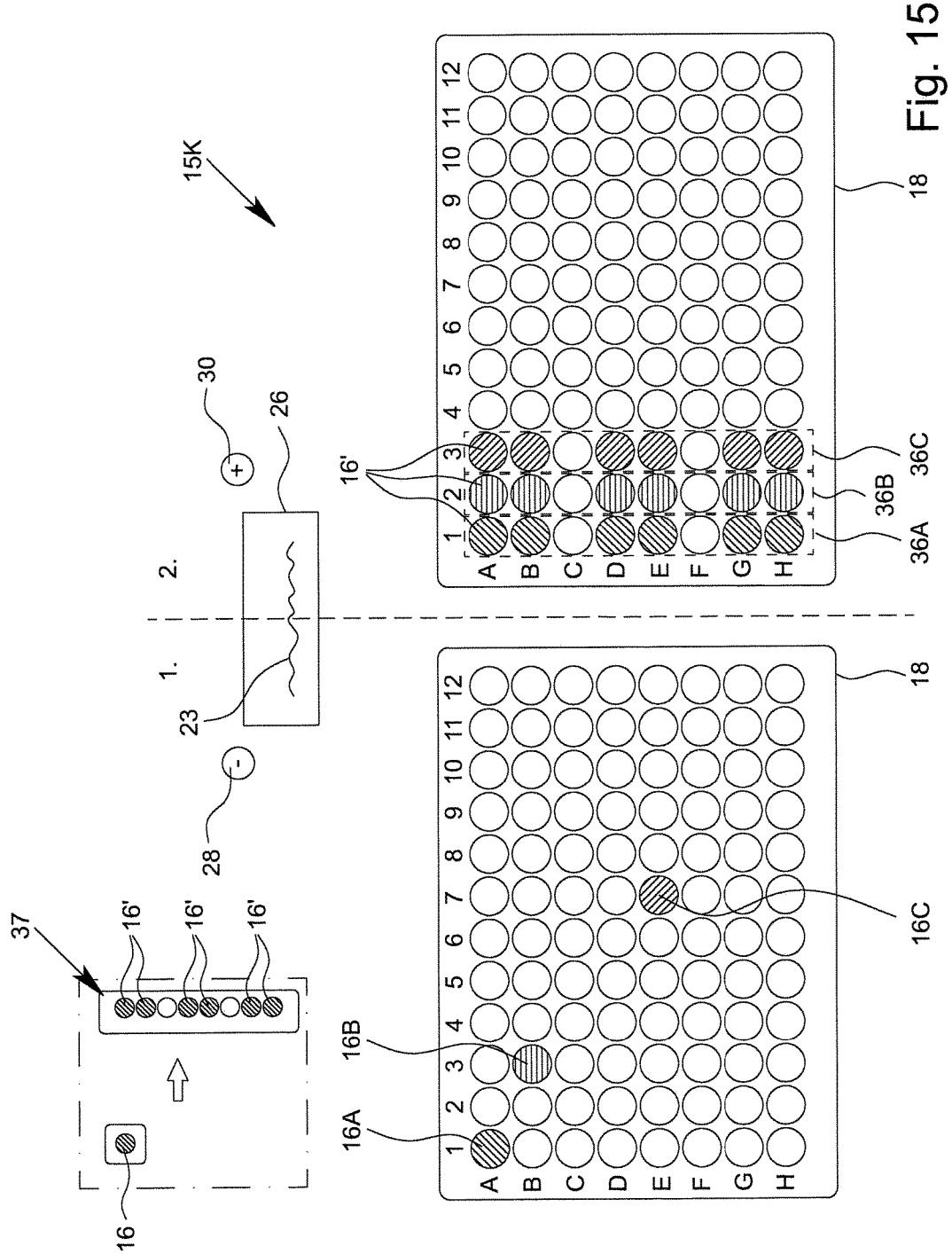
FIG. 15 shows a schematic illustration of a first example of an eleventh configuration interface of the proposed control unit.

FIG. 15 shows a schematic illustration of an eleventh configuration interface 15K of the proposed control unit 1. A transfer pattern 37 is pre-definable in the configuration interface 15K or in a separate configuration interface. In the transfer pattern 37 illustrated in FIG. 15, six target receptacle unit equivalents 16', which are arranged in a column, are assigned to a source receptacle unit equivalent 16, wherein a non-assigned receptacle unit equivalent is arranged after the first two target receptacle unit equivalents 16', which are located one below another. The same applies for the next two target receptacle unit equivalents 16', which are located one below another.

In the configuration interface 15K, multiple, specifically three source receptacle unit equivalents 16A to 16C are now selected and displayed on the first side. On the basis of the predefined transfer pattern 37 one subgroup 36A to 36C of at least one, specifically six target receptacle unit equivalent(s) 16' is assigned to each selected source receptacle unit equivalent 16A to 16C, such that the arrangement and number of the assigned target receptacle unit equivalents 16' of each subgroup 36A to 36C corresponds to the arrangement and number of the receptacle unit equivalents 16 of the transfer pattern 37.

Figure 16:
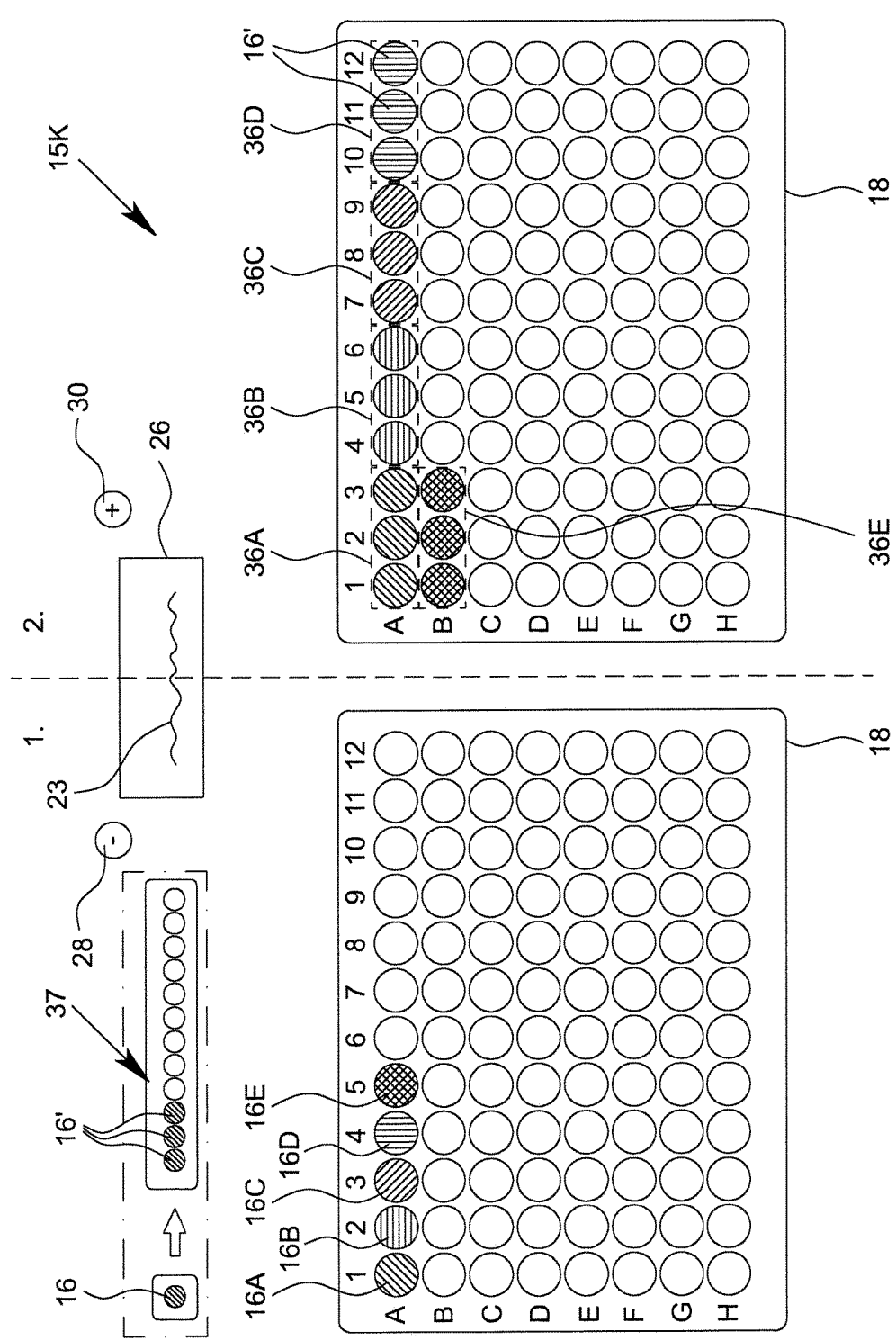
FIG. 16 shows a schematic illustration of a second example of the eleventh configuration interface of the proposed control unit.

In the example illustrated in FIG. 16, a transfer pattern 37 is predefined, according to which three target receptacle unit equivalents 16', which are arranged in one row adjacent to one another, are assigned to one source receptacle unit equivalent 16. In this example, five source receptacle unit equivalents 16A to 16C are selected and displayed in the configuration interface 15K on the first side. A subgroup 36A to 36E of precisely three target receptacle unit equivalents 16', which are arranged in one row adjacent to one another, is assigned to each selected source receptacle unit equivalent 16A to 16E on the basis of the predefined transfer pattern 37, such that the arrangement and number of the assigned target receptacle unit equivalents 16' of each subgroup 36A to 36E corresponds to the arrangement and number of the receptacle unit equivalents 16 of the transfer pattern 37.

Figure 17:
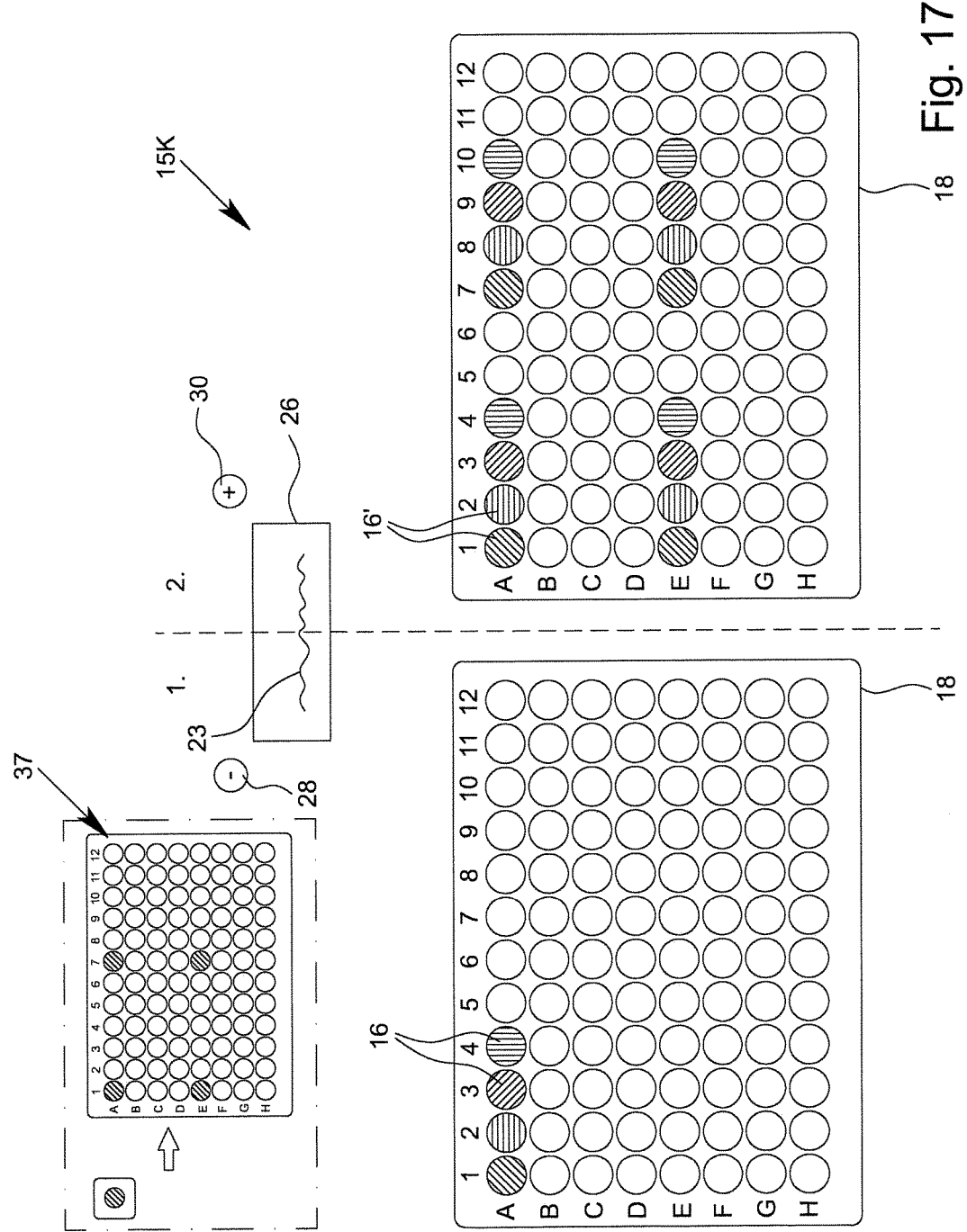
FIG. 17 shows a schematic illustration of a third example of the eleventh configuration interface of the proposed control unit

FIG. 17 illustrates a further example of a predefined transfer pattern 37 and how it is applied to four source receptacle unit equivalents 16.

However, it is also possible to predefine a transfer pattern 37, which assigns multiple, for example four, source receptacle unit equivalents 16 in each case to one subgroup 36 of multiple, for example eight, target receptacle unit equivalents 16'. In this case, however, the arrangement and number of the assigned target receptacle unit equivalents 16' of a subgroup 36 does not correspond to the arrangement and number of the receptacle unit equivalents 16 of the transfer pattern 37. Rather, the selected source receptacle unit equivalents 16 are simultaneously assigned multiple target receptacle unit equivalents 16' on the basis of the transfer pattern 37 such that the arrangement and number of the target receptacle unit equivalents 16' corresponds as a whole to the arrangement and number of the receptacle unit equivalents 16 of the transfer pattern 37.

FIG. 18 shows a schematic illustration of a twelfth configuration interface 15M of the proposed control unit 1. Firstly, all source receptacle unit equivalents 16 were marked in the configuration interface 15L on the first side. An electronically stored selection pattern was then loaded, preferably in a buffer memory. Using the context menu 32 or also in another manner, which is preferably provided in the configuration interface 15L, it can preferably be selectable or selected as an option 33 that the source receptacle unit equivalents 16 are selected on the basis of the loaded selection pattern. The selection pattern is preferably displayable in the configuration interface 15L. On the basis of the assignment of the illustrated selection pattern to source receptacle unit equivalents 16, they are then selected.

For example, column and row specifications of the selected source receptacle unit equivalents 16 can be the selection pattern. However, volume specifications having column and row specifications can also be stored, wherein the column/row combinations which have a positive volume specification identify source receptacle unit equivalents 16 to be selected. The source receptacle unit equivalents 16 having the same column and row specification are displayed in the configuration interface 15L.

The selection pattern can be stored in a file, for example, as a list, and can be opened by means of the control unit 1 and loaded in a buffer memory.

A further aspect of the present invention, which is also implementable independently, is not shown. According to this aspect, multiple source receptacle unit equivalents 16 of a source pipetting unit equivalent 18 are selectable. The selected source receptacle unit equivalents 16 are displayable in a configuration interface 15. The selected source receptacle unit equivalents 16 can be divided into at least two subgroups and these subgroups are successively assignable to multiple target receptacle unit equivalents 16' of a target pipetting unit equivalent 18. In this case, all source receptacle unit equivalents 16 of each subgroup are simultaneously assignable to the respective target receptacle unit equivalents 16'.

Transfer parameters 23 are thus assigned to the selected source receptacle unit equivalents 16 and their assigned target receptacle unit equivalents 16' such that in each case the corresponding transfer volume is transferable from the receptacle units 5 corresponding to the selected source receptacle unit equivalents 16 into the receptacle units 5 corresponding to the assigned target receptacle unit equivalents 16'.

In this case, the assigned target receptacle unit equivalents 16' are displayable in the same configuration interface 15 as the selected source receptacle unit equivalents 16.

A further aspect of the present invention, which is also implementable independently, is not shown. According to this aspect, the steps which the pipetting machine 2 carries out can be recorded and electronically stored, for example, as a report, preferably in an editable electronic file. Such a report or such a recording can be initiated and/or ended automatically or manually via a control command or the configuration interface 15. In addition to the individually performed steps or chronological sequences, such a report can also comprise transfer parameters 23, the positions or paths of the pipetting device 4, and/or time specifications, for example of the performance.

Such a report or a synopsis thereof can preferably be electronically transmitted, for example, to a computer, a smart phone, a tablet, etc. The transmission can take place, for example, during the performance of steps of the pipetting machine 2, after ending a coherent step sequence, in the event of disturbances or status changes of the control unit 1 and/or the pipetting machine 2. The transmission can be performed, for example, via wireless technologies, preferably as an electronic message, such as an email or SMS. It is also possible to transmit a message about the performance of steps by means of the pipetting machine 2 without a report.

The above-described aspects are preferably combinable with one another. Furthermore, it can be provided that the principles explained in conjunction with the configuration interfaces 15B to 15L are selectable as different options and/or by means of one or more context menus 32 in the same configuration interface. In particular virtual switches, checkboxes, drop-down menus, soft buttons, or the like can be provided for this purpose. Furthermore, it is preferable for both the receptacle unit equivalents 16A to 16F to be selectable and also the context menu 32 to be able to be generated and, in this way or in another way, one or more options 33 to be selectable and/or configurable in the same configuration interface 15B to 15L, preferably wherein one or more volume difference(s), volumes, target volumes, and/or the combination, the division, or a changed arrangement are definable, settable, or activatable.

The above-described aspects are in particular successively applicable or executable. Thus, for example, multiple non-bundled source receptacle unit equivalents 16A to 16G can firstly be selected and indicated as bundled receptacle unit equivalents. The indicated receptacle unit equivalents can then, for example, be rotated or reflected and can then be assigned in this arrangement, preferably multiple times, to target receptacle unit equivalents 16'.

The present invention also relates to a method for controlling the pipetting machine 2 having the control unit 1, wherein the above-described principles are carried out alone or in combination. For this purpose, an input by means of the input unit 10 is preferably interpreted by the control unit 1 such that selectable receptacle unit equivalents 16, 16' are selected partially, individually, or in groups, in particular by movement of the selection tool 22 and an input during this and/or following thereupon, for example, by means of a switch or button. The control unit 1 preferably interprets this as a selection of the respective receptacle unit equivalent 16, 16' or a corresponding first or second group 27, 29 and preferably executes individual steps or a combination of steps, of which it has been previously been described that the control unit 1 is suitable for this purpose.

Furthermore, it is preferable for the method to comprise the control of the pipetting machine 2. For this purpose, it can be provided that the control unit 1 controls the different selections of receptacle unit equivalents 16, 16', particularly preferably in the respective chronological sequence of the selection and in consideration of the respective options 33 active during the selection, in that the control unit 1 generates machine commands and transmits them to the pipetting machine 2. In this way, in particular actuators 3A to 3C of the pipetting machine 2 are controlled such that the previously configured receiving and dispensing of the respective transfer volumes from or into the receptacle units 5 are caused.

What is claimed is:

1. A control unit for controlling a pipetting machine, wherein:
   the control unit is programmed to control at least one actuator of a pipetting machine for moving a pipetting device of said pipetting machine between receptacle units for receiving liquids to be pipetted, and for dispensing liquids to be pipetted,
   the control unit has an input unit and a display unit on which multiple configuration interfaces are displayable,
   the control unit is programmed to cause multiple graphic receptacle unit equivalents, each of which corresponds to and represents at least one receptacle unit, to be displayed on the display unit in a configuration interface, and
   the control unit is programmed in a manner to perform the following operations so as to enable transfer patterns to be created, changed, and assigned to multiple target receptacle unit equivalents:
      selecting, in the configuration interface, multiple graphic receptacle unit equivalents as a first group of source receptacle unit equivalents,
      displaying, in the configuration interface, upon selection of the first group of source receptacle unit equivalents, a graphic representation of the first group of selected source receptacle unit equivalents, wherein the graphic representation of the first group of selected source receptacle unit equivalents is separate from the displayed source receptacle unit equivalents and depicts a transfer pattern,
      changing, in the configuration interface, the graphic representation of the first group of selected source receptacle unit equivalents with respect to at least one of the number and arrangement of the first group of selected source receptacle unit equivalents,
      selecting, in the configuration interface, by use of the input unit and the graphic representation of the first group of selected source receptacle unit equivalents, a second group of graphic receptacle unit equivalents as target receptacle unit equivalents,
      simultaneously assigning the selected first group of source receptacle unit equivalents to the second group of target receptacle unit equivalents, such that at least one of the arrangement and number of the assigned second group of target receptacle unit equivalents differs from at least one of the arrangement and number of the selected first group of source receptacle unit equivalents,
      assigning, by selection of the second group of target receptacle unit equivalents, transfer parameters to the first group of selected source receptacle unit equivalents and their assigned second group of target receptacle unit equivalents such that a respective transfer volume corresponding to the respective transfer parameter is transferable from the receptacle units corresponding to the selected first group of source receptacle unit equivalents into the receptacle units corresponding to the assigned second group of target receptacle unit equivalents,
      displaying the assigned second group of target receptacle unit equivalents in the same configuration interface as the selected first group of source receptacle unit equivalents, and controlling said at least one actuator for moving said pipetting device between receptacle units for receiving or dispensing liquids to be pipetted in response to selecting of one of the displayed target receptacle unit equivalents.

2. The control unit as claimed in claim 1, wherein the graphic receptacle unit equivalents are arranged in rows and columns and the control unit is programmed such that the selected source receptacle unit equivalents of the first group are simultaneously assignable to the target receptacle unit equivalents of the second group such that the arrangement of the assigned second group of target receptacle unit equivalents corresponds to at least one of a reflection, rotation, row-by-row or column-by-column exchange, and a row-by-row or column-by-column shift of the arrangement of the selected first group of source receptacle unit equivalents.

3. The control unit as claimed in claim 1, wherein the control unit is programmed to assign selected unbundled source receptacle unit equivalents of the first group to target receptacle unit equivalents of the second group such that the assigned target receptacle unit equivalents of the second group are arranged in a bundled manner.

4. The control unit as claimed in claim 1, wherein the control unit is programmed such that the source receptacle unit equivalents are selectable by use of an electronically stored selection pattern that is displayable in the configuration interface.

5. The control unit as claimed in claim 1,
wherein the selected source receptacle unit equivalents of the first group are dividable into at least two subgroups that are successively assignable to the target receptacle unit equivalents of the second group and
wherein all source receptacle unit equivalents of each subgroup are simultaneously assignable to the respective target receptacle unit equivalents of the second group.

6. The control unit of claim 1, wherein the control unit is programmed in a manner to perform the following operation:
generating or activating a context menu in the configuration interface for virtual modification of at least one of the arrangement and number of the selected first group of source receptacle unit equivalents.

7. A pipetting machine having the control unit as claimed in claim 1, wherein the pipetting machine has the at least one actuator for moving a pipetting device between receptacle units for liquids to be pipetted for at least one of receiving liquid and dispensing liquid, and wherein the at least one actuator is controllable by the control unit.

8. A method for controlling a pipetting machine for controlling at least one actuator for moving a pipetting device of a pipetting machine between receptacle units of said pipetting machine for liquids to be pipetted, for receiving liquids to be pipetted, and for dispensing liquids to be pipetted, having a control unit having an input unit and a display unit on which multiple configuration interfaces are displayable, and wherein multiple graphic receptacle unit equivalents, each of which corresponds to and represents at least one receptacle unit, are displayable on the display unit in a configuration interface, the following steps being performed in a manner enabling transfer patterns to be created and changed, and assigned to multiple target receptacle unit equivalents:
selecting, in the configuration interface, multiple graphic receptacle unit equivalents as a first group of source receptacle unit equivalents,
displaying, in the configuration interface, upon selection of the first group of source receptacle unit equivalents, a graphic representation of the first group of selected source receptacle unit equivalents, wherein the graphic representation of the first group of selected source receptacle unit equivalents is separate from the displayed source receptacle unit equivalents and depicts a transfer pattern,
changing, in the configuration interface, the graphic representation of the first group of selected source receptacle unit equivalents with respect to at least one of the number and arrangement of the first group of selected source receptacle unit equivalents,
selecting, in the configuration interface, by use of the input unit and the graphic representation of the first group of selected source receptacle unit equivalents, a second group of graphic receptacle unit equivalents as target receptacle unit equivalents,
simultaneously assigning the selected first group of source receptacle unit equivalents to the second group of target receptacle unit equivalents, such that at least one of the arrangement and number of the assigned second group of target receptacle unit equivalents differs from at least one of the arrangement and number of the selected first group of source receptacle unit equivalents,
assigning, by selection of the second group of target receptacle unit equivalents, transfer parameters to the first group of selected source receptacle unit equivalents and their assigned second group of target receptacle unit equivalents such that a respective transfer volume corresponding to the respective transfer parameter is transferable from the receptacle units corresponding to the selected first group of source receptacle unit equivalents into the receptacle units corresponding to the assigned second group of target receptacle unit equivalents,
displaying the assigned second group of target receptacle unit equivalents in the same configuration interface as the selected first group of source receptacle unit equivalents, and
controlling said at least one actuator for moving said pipetting device between receptacle units for receiving or dispensing liquids to be pipetted in response to selecting of one of the displayed target receptacle unit equivalents.

9. The method as claimed in claim 8, wherein the graphic receptacle unit equivalents are arranged in rows and columns and the selected source receptacle unit equivalents of the first group are simultaneously assigned to the target receptacle unit equivalents of the second group such that the arrangement of the assigned second group of target receptacle unit equivalents corresponds to a reflection, rotation, row-by-row or column-by-column exchange, and/or row-by-row or column-by-column shift of the arrangement of the selected first group of source receptacle unit equivalents.

10. The method as claimed in claim 8, wherein selected unbundled source receptacle unit equivalents of the first group are simultaneously assigned to target receptacle unit equivalents of the second group such that the assigned second group of target receptacle unit equivalents are arranged in a bundled manner.

11. The method as claimed in claim 8, wherein the first group of source receptacle unit equivalents are selected by use of an electronically stored selection pattern and the selection pattern is displayed in the configuration interface.

12. The method as claimed in claim 8,
wherein the selected first group of source receptacle unit equivalents is divided into at least two subgroups that are successively assigned to the second group of target receptacle unit equivalents and
all source receptacle unit equivalents of each subgroup are simultaneously assigned to the respective target receptacle unit equivalents.

13. The method as claimed in claim 8, wherein a context menu is generated or activated in the configuration interface for virtual modification of at least one of the arrangement and number of the selected first group of source receptacle unit equivalents.

* * * * *